(12) United States Patent
Duer et al.

(10) Patent No.: US 10,159,685 B2
(45) Date of Patent: Dec. 25, 2018

(54) VASCULAR CALCIFICATION

(71) Applicants: Cambridge Enterprise Limited, Cambridge, Cambridgeshire (GB); King's College London, London (GB)

(72) Inventors: Melinda Duer, Cambridge (GB); David Reid, Cambridge (GB); Catherine Shanahan, London (GB)

(73) Assignees: Cambridge Enterprise Limited, Cambridge (GB); King's College London, London (GB)

( * ) Notice: Subject to any disclaimer, the term of this patent is extended or adjusted under 35 U.S.C. 154(b) by 0 days.

(21) Appl. No.: 15/624,299

(22) Filed: Jun. 15, 2017

(65) Prior Publication Data
US 2017/0360809 A1 Dec. 21, 2017

(30) Foreign Application Priority Data

Jun. 15, 2016 (GB) .................................. 1610400.2

(51) Int. Cl.
| | | |
|---|---|---|
| *A61K 31/47* | (2006.01) | |
| *A61K 31/50* | (2006.01) | |
| *A61K 31/55* | (2006.01) | |
| *A61K 31/65* | (2006.01) | |
| *A61K 45/06* | (2006.01) | |
| *A61K 31/166* | (2006.01) | |
| *A61K 31/454* | (2006.01) | |
| *A61K 31/473* | (2006.01) | |
| *A61K 31/502* | (2006.01) | |
| *A61K 31/506* | (2006.01) | |
| *A61K 31/519* | (2006.01) | |
| *A61K 31/522* | (2006.01) | |
| *A61K 31/554* | (2006.01) | |
| *A61K 31/4184* | (2006.01) | |
| *A61K 31/4709* | (2006.01) | |
| *A61K 31/5025* | (2006.01) | |

(52) U.S. Cl.
CPC ............ *A61K 31/65* (2013.01); *A61K 31/166* (2013.01); *A61K 31/4184* (2013.01); *A61K 31/454* (2013.01); *A61K 31/473* (2013.01); *A61K 31/4709* (2013.01); *A61K 31/502* (2013.01); *A61K 31/506* (2013.01); *A61K 31/5025* (2013.01); *A61K 31/519* (2013.01); *A61K 31/522* (2013.01); *A61K 31/55* (2013.01); *A61K 31/554* (2013.01); *A61K 45/06* (2013.01); *A61K 31/47* (2013.01); *A61K 31/50* (2013.01)

(58) Field of Classification Search
CPC ........ A61K 31/65; A61K 31/50; A61K 31/55; A61K 31/47
USPC ....... 514/152, 212.06, 218, 234.2, 248, 309, 514/312
See application file for complete search history.

(56) References Cited

U.S. PATENT DOCUMENTS

| | | |
|---|---|---|
| 6,706,290 B1 | 3/2004 | Kajander et al. |
| 2006/0083727 A1 | 4/2006 | Kajander et al. |
| 2010/0292183 A1 | 11/2010 | Madasamy |
| 2013/0338118 A1 | 12/2013 | Gilmer et al. |
| 2015/0366882 A1 | 12/2015 | Altschul et al. |

FOREIGN PATENT DOCUMENTS

| | | |
|---|---|---|
| WO | WO 1999/011645 A1 | 3/1999 |
| WO | WO 2000/001238 A1 | 1/2000 |
| WO | WO 2005/089259 A2 | 9/2005 |
| WO | WO 2006/019844 A1 | 2/2006 |
| WO | WO 2012/151701 A1 | 11/2012 |
| WO | WO 2016/051213 A1 | 4/2016 |
| WO | WO 2017/216563 A1 | 12/2017 |

OTHER PUBLICATIONS

PCT/GB2017/051744 International Search Report and Written Opinion dated Sep. 11, 2017.
Hecht, et al., "The matrix metalloproteinases 2 and 9 initiate uraemic vascular calcifications," *Nephrol Dial Transplants*, 31:789-797 (2016).
Qin, et al., "Matrix Metalloproteinase Inhibition Attenuates Aortic Calcification," *Arterioscler Thromb Vasc Biol.*, 26:1510-1516 (2006) available at <https://www.atybaba.org> retrieved on Aug. 25, 2017.
Salo et al., "Chemically Modified Tetracyclines (CMT-3 and CMT-8) Enable Control of the Pathological Remodellation of Human Aortic Valve Stenosis via MMP-9 and VEGF Inhibition," *International Journal of Cardiology*, 111(3):358-364, (2006).
Shahzad et al., "Minocycline Reduces Plaque Size in Diet Induced Atherosclerosis via p27KIP1," *Atherosclerosis*, 219(1):74-83, (2011).
Tao et al., "Minocycline Protects Cardiac Myocytes Against Simulated Ischemia-Reperfusion Injury by Inhibiting Poly(ADP-ribose)Polymerase-1," *J. Cardiovasc. Pharmacol.*, 56(6):659-668, (2010).
Szabo et al., "Cardioprotective Effects of Poly(ADP-ribose) Polymerase Inhibition," *Pharmacological Research*, 52(1):34-43, (2005).
Szenczi et al., "Poly(ADP-ribose) Polymerase Regulates Myocardial Calcium Handling in Doxorubicin-Induced Heart Failure," *Biochemical Pharmacology*, 69(5):725-732, (2005).
Pacher et al., "Role of Poly(ADP-ribose) Polymerase 1 (PARP-1) in Cardiovascular Diseases: The Therapeutic Potential of PARP Inhibitors," *Cardiovasc. Drug Rev.*, 25(3):235-260, (2007).
Meloche et al., "Role for DNA Damage Signaling in Pulmonary Arterial Hypertension," *Circulation*, 129(7):786-797 (2013).
Booz et al., "PARP Inhibitors and Heart Failure—Translational Medicine Caught in the Act," *Congestive Heart Failure*, 13(2):105-112, (2007).
GB Search Report from application GB1610400.2 dated Feb. 28, 2017.

(Continued)

*Primary Examiner* — Kevin E Weddington
(74) *Attorney, Agent, or Firm* — Alston & Bird LLP

(57) ABSTRACT

The invention relates to the use of a poly(ADP ribose) polymerase (PARP) inhibitor and/or a tetracycline, for treating, preventing or ameliorating medial vascular calcification, and to pharmaceutical compositions comprising PARP inhibitors or tetracycline.

13 Claims, 23 Drawing Sheets
(7 of 23 Drawing Sheet(s) Filed in Color)

(56) References Cited

OTHER PUBLICATIONS

GB Search Report from application GB1610400.2 dated May 2, 2017.
Martel, et al., "Purported nanobacteria in human blood as calcium carbonate nanoparticles," *PNAS*, vol. 105, No1. 14, pp. 5549-5554, (Apr. 8, 2009).
Hopkin, "Nanobacteria theory takes a hit," *Nature*, published online Apr. 17, 2008, doi:10.1038/news.2008.762 <https://ww.nature.com/news/2008/080417/full/news.2008.762.html.
Schlieper, et al., "A red herring in vascular calcification: 'nanobacteria' are protein-mineral complexes involved in biomineralization," *Nephrol Dial Transplant*, 26: 3436-3439, (2001).

VASCULAR CALCIFICATION

CROSS-REFERENCE TO RELATED APPLICATIONS

This application claims the benefit of United Kingdom (GB) Application No. 1610400.2, filed Jun. 15, 2016, which is herein incorporated by reference in its entirety for all purposes.

FIELD OF THE INVENTION

The present invention relates to vascular calcification, and in particular to compounds useful for treatment of diseases associated with excessive and/or inappropriate vascular calcification. The invention is especially concerned with treating medial vascular calcification or intimal atherosclerotic calcification. The invention extends to pharmaceutical compositions and methods of treating excessive and/or inappropriate (i.e. medial) vascular calcification.

BACKGROUND

Vascular calcification is associated with a range of diseases, and can be broadly separated into three distinct types, namely (1) intimal atherosclerotic calcification, which is calcification of the tunica intima, and includes atherosclerosis and the associated inflammation; (2) valvular calcific aortic stenosis, which is calcification of the aortic valve; and (3) arterial medial calcification, which is calcification of the tunica media, see Demer and Tintut "Vascular Calcification", Circulation, 2008; 117, 2938-2948.

The tunica media is the middle layer of an artery or vein and is made up of smooth muscle cells and elastic tissue.

As shown in FIG. 28A, atherosclerotic calcification is eccentric and leads to lumen deformation. The deformation of the lumen is caused by a lipoprotein deposition 3, due to cholesterol-laden white blood cells (foam cells), covered by a fibrous intimal cap 4. Calcification 1 occurs throughout the atherosclerotic lesion, including in the cap 4, and focal elastinolysis 2 occurs in the tunica media adjacent to the lipoprotein deposition 3. Vessel stiffening is caused by atherosclerotic calcification.

Conversely, as shown in FIG. 28B, medial calcification is concentric. Accordingly, calcification 1 and elastinolysis occurs throughout the tunica media. Vessel stiffening is also caused by medial calcification.

At the molecular level, calcification is the formation and binding of mineral particles into the extracellular matrix. Work over the last 20 years has demonstrated that vascular calcification is a cell-mediated process with similarities to developmental osteo\chondrogenesis. Calcification results in stiffening of the matrix, which is essential for bone, but with detrimental consequences for the mechanical properties of vascular tissue.

Mönckeberg's arteriosclerosis, otherwise known as medial calcific sclerosis, is the most common variety of medial calcification. Furthermore, calcific uremic arteriolopathy (CUA), otherwise known as calciphylaxis, is a severely morbid and life-threatening form of medial vascular calcification that leads to cutaneous necrosis and panniculitis.

The reduced aortic and arterial elastance, caused by vascular calcification, impairs cardiovascular hemodynamics. This can result in hypertension, aortic stenosis, cardiac hypertrophy, myocardial and lower-limb ischemia and congestive heart failure. In particular, vascular calcification is a leading risk factor for cardiovascular disease.

Vascular calcification is also commonly associated with diabetes mellitus I, diabetes mellitus II, chronic renal disease, ageing, hyperparathyroidism, vitamin D disorders, vitamin K deficiency, osteoporosis, Kawasaki disease, arterial calcification due to deficiency of CD73 (ACDC), generalized arterial calcification of infancy (GACI), idiopathic basal ganglia calcification (IBGC), pseudoxanthoma elasticum (PXE), rheumatoid arthritis, Singleton-Merten syndrome, β-thalassemia and warfarin use.

Accordingly, there is a need for compounds which can be used to treat, prevent or ameliorate diseases associated with excessive and/or inappropriate vascular calcification, and in particular medial vascular calcification or intimal atherosclerotic calcification.

SUMMARY

In one aspect, provided is a method of treating, preventing or ameliorating medial vascular calcification or intimal atherosclerotic calcification in a subject, the method comprising administering to a subject in need of such treatment, a therapeutically effective amount of a poly(ADP ribose) polymerase (PARP) inhibitor and/or a tetracycline, or a pharmaceutically acceptable salt or solvate thereof.

Some such methods are for treating, preventing or ameliorating medial vascular calcification. Optionally, the method is a method of treating, preventing or ameliorating Mönckeberg's arteriosclerosis or calcific uremic arteriolopathy (CUA). Optionally, the subject is suffering from chronic kidney disease, diabetes, ageing, hyperparathyroidism, hyperphosphatemia, a vitamin D disorder, a vitamin K disorder, osteoporosis, Kawasaki disease, arterial calcification due to deficiency of CD73 (ACDC), generalized arterial calcification of infancy (GACI), idiopathic basal ganglia calcification (IBGC), pseudoxanthoma elasticum (PXE), rheumatoid arthritis, Singleton-Merten syndrome and/or β-thalassemia.

Some such methods are methods of treating, preventing or ameliorating intimal atherosclerotic calcification. Optionally, the subject has an Agatston score of at least 20, at least 40, at least 60, at least 80 or at least 100.

In some such methods, the PARP inhibitor and/or tetracycline is a PARP inhibitor and is selected from a group consisting of: olaparib; rucaparib; niraparib; veliparib; talazoparib; minocycline; cilostazol; N-(6-Oxo-5,6-dihydrophenanthridin-2-yl)-(N,N-dimethylamino)acetamide hydrochloride (PJ34); 3-aminobenzamide (3-AB); and 3,4-dihydro-5-[4-(1-piperidinyl)butoxyl]-1(2H)-isoquinolinone (DPQ), or a derivative thereof, or a derivative thereof. Optionally, the PARP inhibitor is selected from a group consisting of olaparib; rucaparib; niraparib; veliparib; talazoparib; minocycline; and cilostazol, or a derivative thereof.

In some such methods, the PARP inhibitor and/or tetracycline is a tetracycline and is selected from a group consisting of: tetracycline; chlortetracycline; oxytetracycline; demeclocycline; lymecycline; meclocycline; metacycline; minocycline; rolitetracycline; doxycycline; tigecycline; clomocycline; and pipacycline. Optionally, the tetracycline is minocycline In some such methods, the PARP inhibitor and/or tetracycline is administered as a daily dose of between 1 mg and 10000 mg or between 2 mg and 2000 mg, between 5 mg and 1000 mg, between 10 mg and 200 mg, between 15 mg and 100 mg or between 20 mg and 50 mg.

In some such methods, the PARP inhibitor and/or tetracycline is administered as two daily doses, wherein each dose is between 1 mg and 5000 mg, between 2 mg and 1000 mg, between 3 mg and 500 mg, between 4 mg and 100 mg, between 5 mg and 50 mg or between 10 mg and 25 mg. Optionally, each dose is between 10 mg and 25 mg.

In another aspect, provided are pharmaceutical compositions for treating medial vascular calcification or intimal atherosclerotic calcification comprising a PARP inhibitor and/or tetracycline, or a pharmaceutically acceptable salt or solvate thereof, and a pharmaceutically acceptable vehicle.

In another aspect, provided are processes for making the pharmaceutical composition, the processes comprising contacting a therapeutically effective amount of a PARP inhibitor and/or tetracycline, or a pharmaceutically acceptable salt or solvate thereof, and a pharmaceutically acceptable vehicle.

BRIEF DESCRIPTION OF THE FIGURES

The patent or application file contains at least one drawing executed in color. Copies of this patent or patent application publication with color drawing(s) will be provided by the Office upon request and payment of the necessary fee.

For a better understanding of the invention, and to show how embodiments of the same may be carried into effect, reference will now be made, by way of example, to the accompanying Figures, in which:—

DETAILED DESCRIPTION

Figure 1A:
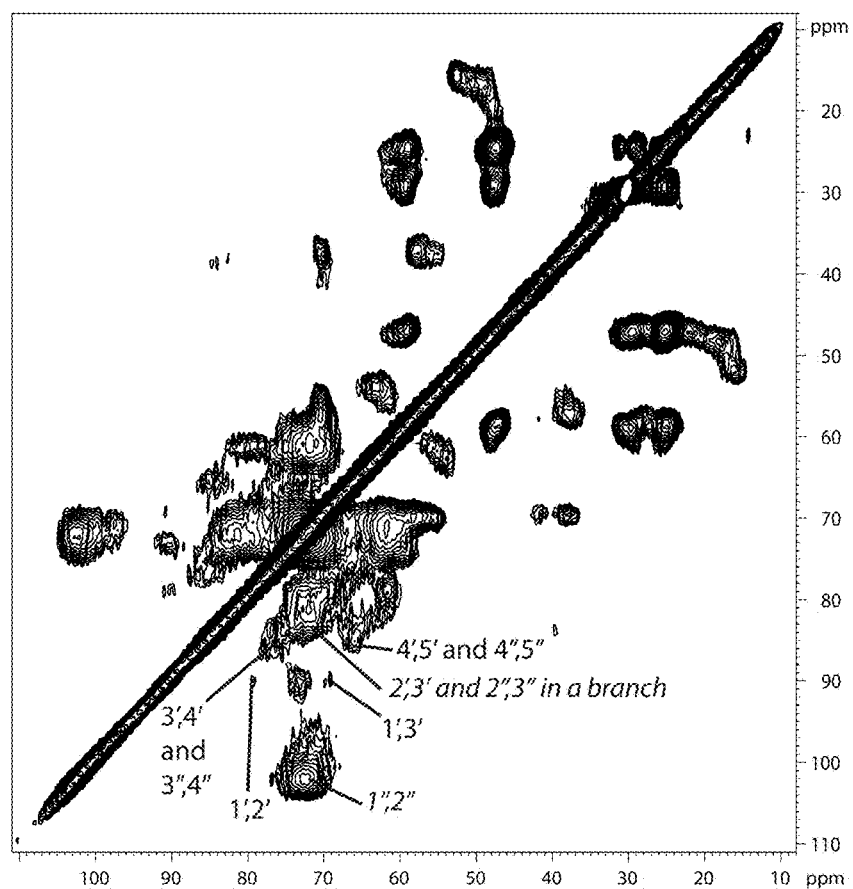
FIG. 1A shows a two-dimensional $^{13}C$-$^{13}C$ correlation NMR spectra of an in vitro human VSMC extracellular matrix after cell lysis and washing of the matrix. Sugar components biosynthesised from glucose are 13C-labelled, as are glycine and proline/hydroxyproline (predominantly present in collagen proteins). In addition to the expected amino acid signals from collagen glycine, proline and hydroxyproline and from collagen glycosylation (primarily O-linked α-glucosyl-β-galactosyl and β-galactosyl) there are clear signals from poly(ADP ribose). Assignments in italic font indicate there are signals from other molecular species overlapping the poly(ADP ribose) signals.

As described in the Examples, the inventors have demonstrated that a range of compounds acting as poly(ADP ribose) polymerase (PARP) inhibitors and the tetracycline class of antibiotics can be used to reduce medial vascular calcification.

Thus, in accordance with a first aspect of the invention, there is provided a poly(ADP ribose) polymerase (PARP) inhibitor and/or a tetracycline, or a pharmaceutically acceptable salt or solvate thereof, for use in treating, preventing or ameliorating medial vascular calcification or intimal atherosclerotic calcification.

According to a second aspect of the invention, there is provided a method of treating, preventing or ameliorating medial vascular calcification or intimal atherosclerotic calcification in a subject, the method comprising administering to a subject in need of such treatment, a therapeutically effective amount of a poly(ADP ribose) polymerase (PARP) inhibitor and/or a tetracycline, or a pharmaceutically acceptable salt or solvate thereof.

Advantageously, the Examples show that the PARP inhibitor and/or the tetracycline inhibits calcification in a dose dependent manner. Furthermore, the Examples show that the PARP inhibitor and/or the tetracycline inhibits calcification of smooth muscle cells, which are present in the tunica media. Preferably, therefore, the PARP inhibitor and/or the tetracycline inhibits calcification of smooth muscle cells present in the tunica media. Preferably, the PARP inhibitor and/or the tetracycline is for use in treating, preventing or ameliorating arterial medial calcification.

Preferably, the PARP inhibitor and/or tetracycline is for use in treating, preventing or ameliorating medial vascular calcification.

Preferably, the PARP inhibitor and/or tetracycline is for use in treating, preventing or ameliorating a disease selected from a group consisting of: Mönckeberg's arteriosclerosis; and calcific uremic arteriolopathy (CUA).

Preferably, the PARP inhibitor and/or tetracycline is for use in treating, preventing or ameliorating medial vascular calcification in a subject suffering from chronic kidney disease, diabetes, ageing, hyperparathyroidism, hyperphosphatemia, a vitamin D disorder, a vitamin K disorder, osteoporosis, Kawasaki disease, arterial calcification due to deficiency of CD73 (ACDC), generalized arterial calcification of infancy (GACI), idiopathic basal ganglia calcification (IBGC), pseudoxanthoma elasticum (PXE), rheumatoid arthritis, Singleton-Merten syndrome and/or β-thalassemia. Preferably, the chronic kidney disease is end-stage renal disease. The diabetes may be diabetes mellitus I. Preferably, the diabetes is diabetes mellitus II. Preferably, the vitamin D disorder is vitamin D toxicity. Preferably, the vitamin K disorder is vitamin K deficiency.

Preferably, the PARP inhibitor and/or tetracycline is for use in treating, preventing or ameliorating medial vascular calcification in a subject being prescribed warfarin.

Preferably, the PARP inhibitor and/or tetracycline is not for use in treating, preventing or ameliorating valvular calcific aortic stenosis, such as calcification of the aortic valve.

Alternatively, the PARP inhibitor and/or tetracycline may be for use in treating, preventing or ameliorating intimal atherosclerotic calcification.

The inventors note that atherosclerotic calcification requires osteogenic differentiation of vascular smooth muscle cells, in other words a specific transformation of the blood vessel cells before it happens. For this reason, there are atherosclerotic plaques that never calcify, no matter how bad they are, and equally others that calcify at an early stage of vascular damage. Accordingly, calcification is not an inevitable part of atherosclerosis, and will only be suffered by a select group of patients. What triggers the cell transformation that causes atherosclerotic calcification is not specifically known, although it is speculated that the control mechanism that prevents calcification in atherosclerosis in general may break down in some patients leading to atherosclerotic calcification.

A patient suffering from atherosclerotic calcification can be identified using a computed tomography (CT) scan. The CT scan can be used to calculate an Agatston score, a pseudo-continuous variable derived from plaque densities and their areas in all coronary arteries, for a patient. Accordingly, a patient with an Agatston score of 0 would have no coronary artery calcification. Preferably, the PARP inhibitor and/or tetracycline is for use in treating atherosclerotic calcification in a patient with an Agatston score of at least 20, more preferably at least 40, at least 60 or at least 80, and most preferably at least too.

Plaque structural stress increases initially with early plaque calcification, and can lead to plaque rupture which can in turn cause a heart attack. Accordingly, the PARP inhibitor and/or tetracycline is for use in treating atherosclerotic calcification in a patient exhibiting early calcification in atherosclerosis. Images of a patient's vascular system could be obtained using virtual-histology intravascular ultrasound (VH-IVUS), and patients exhibiting early calcification could be identified therefrom.

Accordingly, the inventors have identified a novel patient group, namely a patient suffering from atherosclerotic calcification, which may be successfully treated using PARP inhibitors. The inventors note that statins are normally used to treat atherosclerosis. However, as shown in Example 9, statins do not treat calcification per se, and so the atherosclerotic calcification would not be treated using statins. In fact, there is some evidence that intimal calcification increases with statin use. Accordingly, the present invention allows the novel patient group to be specifically and purposefully treated using PARP inhibitors.

Preferably, the PARP inhibitor and/or tetracycline is for use in treating, preventing or ameliorating atherosclerotic calcification in a subject suffering from hypertension, aortic stenosis, cardiac hypertrophy, myocardial and lower-limb ischemia and congestive heart failure.

The PARP inhibitor may be selected from a group consisting of: olaparib; rucaparib; niraparib; veliparib; talazoparib; minocycline; cilostazol; N-(6-Oxo-5,6-dihydrophenanthridin-2-yl)-(N,N-dimethylamino)acetamide hydrochloride (PJ34); 3-aminobenzamide (3-AB); and 3,4-dihydro-5-[4-(1-piperidinyl)butoxyl]-1(2H)-isoquinolinone (DPQ), or a derivative thereof.

Preferably, the PARP inhibitor is capable of inhibiting PARP produced by a mammalian cell.

Preferably, the PARP inhibitor comprises olaparib; rucaparib; niraparib; veliparib; talazoparib; minocycline; or cilostazol; or a derivative thereof. Alternatively, the PARP inhibitor comprises PJ34; minocycline; 3-AB; or DPQ.

The derivative of minocycline may have general formula [II]:

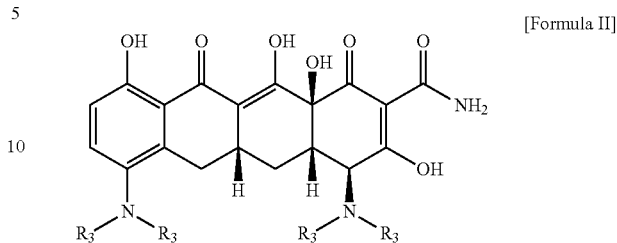

[Formula II]

wherein, each $R_3$ is a $C_{1-3}$ alkyl.

The derivative of veliparib may have general formula [III]:

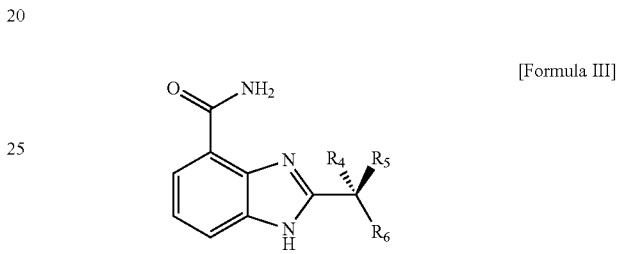

[Formula III]

wherein, $R_4$ is a $C_{1-3}$ alkyl; and $R_5$ and $R_6$ together with the carbon atom to which they are bonded form a five or six membered heterocycyl group.

Preferably, $R_4$ is methyl. Preferably, $R_5$ and $R_6$ together with the carbon atom to which they are bonded form a five membered heterocycyl group. More preferably, the heterocycyl group is pyrrolidine or tetrahydrofuran.

The derivative of niraparib may have general formula [IV]:

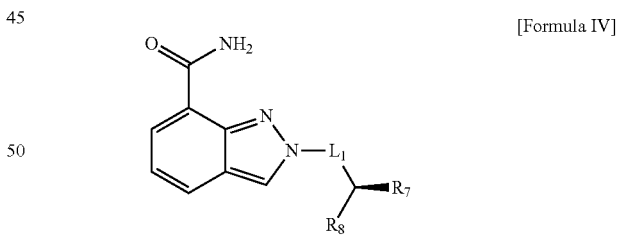

[Formula IV]

wherein, $L_1$ is a six membered aryl or heteroaryl group; and $R_7$ and $R_8$ together with the carbon atom to which they are bonded form a five or six membered heterocycyl group.

Preferably, $L_1$ is a phenyl group. Preferably, $L_1$ is substituted in the para positions. Preferably, $R_7$ and $R_8$ together with the carbon atom to which they are bonded form a six membered heterocycyl group. More preferably, the heterocycyl group is piperidine, tetrahydropyran or thiane.

The derivative of rucaparib may have general formula [V]:

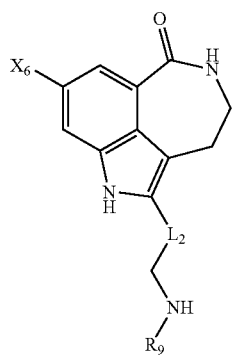

[Formula V]

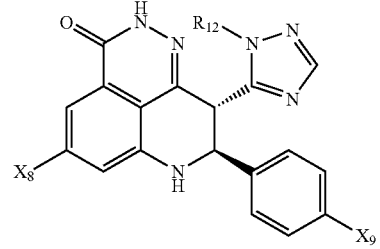

[Formula VII]

wherein, $X_6$ is a halogen;
$L_2$ is a six membered aryl or heteroaryl group; and
$R_9$ is a $C_{1-3}$ alkyl.

Preferably, $X_6$ is fluorine, chlorine or bromine, more preferably fluorine or chlorine, most preferably fluorine. Preferably, $L_2$ is a phenyl group. Preferably, $L_2$ is substituted in the para positions. Preferably, $R^9$ is methyl.

The derivative of olaparib may have general formula [VI]:

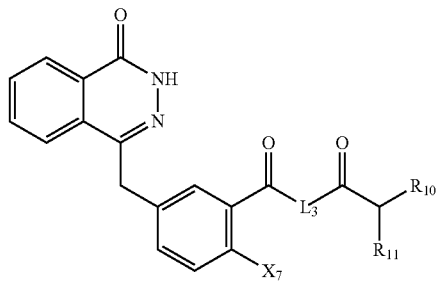

[Formula VI]

wherein, $X_7$ is a halogen;
$L_3$ is a six membered cycloalkyl or heterocyclyl group; and
$R_{10}$ and $R_{11}$ together with the carbon atom to which they are bonded form a 3 to 6 membered cycloalkyl group.

Preferably, $X_7$ is fluorine, chlorine or bromine, more preferably fluorine or chlorine, most preferably fluorine. Preferably, $L_3$ is a six membered heterocyclyl group. More preferably, $L_3$ is piperazine, morpholine, thiomorpholine, dioxane or dithiane. More preferably, $L_3$ is

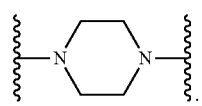

Preferably, $R_{10}$ and $R_{11}$ together with the carbon atom to which they are bonded form cyclopropyl, cyclobutyl or cyclopentyl, more preferably cyclopropyl or cyclobutyl, and most preferably cyclopropyl.

The derivative of talazoparib may have the general formula [VII]:

chiometrics is a halogen;
$X_9$ is halogen; and
$R_{12}$ is a $C_{1-3}$ alkyl.

Preferably, $X_8$ is fluorine, chlorine or bromine, more preferably fluorine or chlorine, most preferably fluorine. Preferably, $X_9$ is fluorine, chlorine or bromine, more preferably fluorine or chlorine, most preferably fluorine. Preferably, $R_{12}$ is methyl.

Figure 9A:
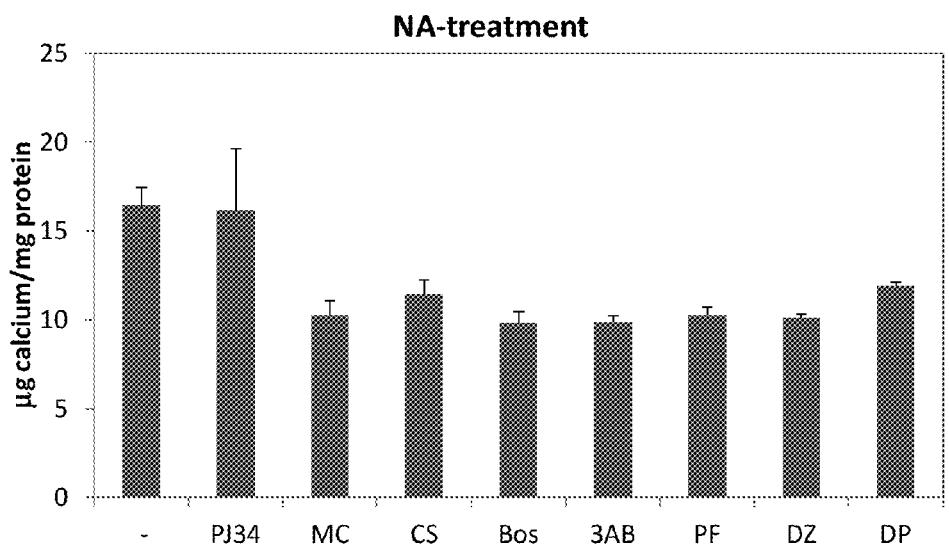
FIGS. 9A and 9B are graphs which normalise the results shown in FIGS. 7A and 7B respectively to give the mass of calcium per mass of protein.
Figure 9B:
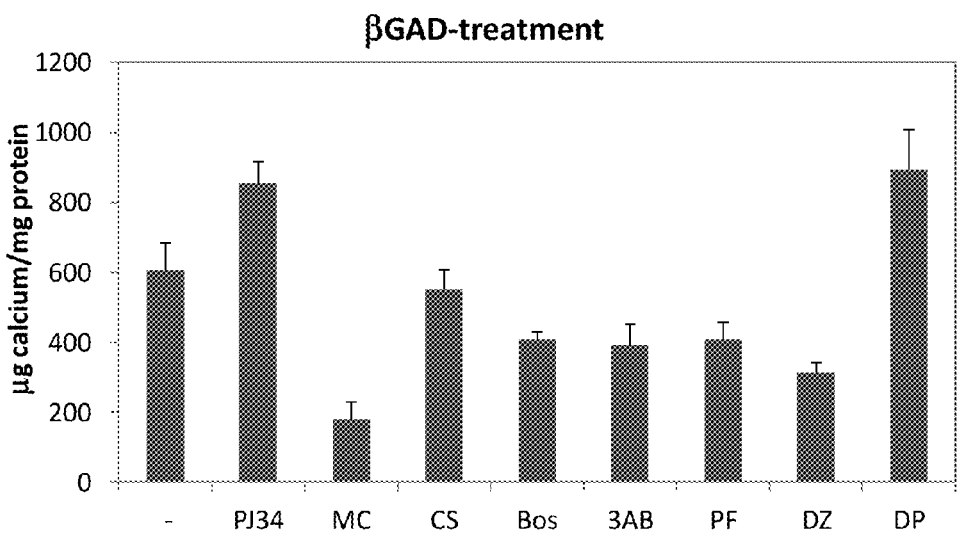
Figure 13:
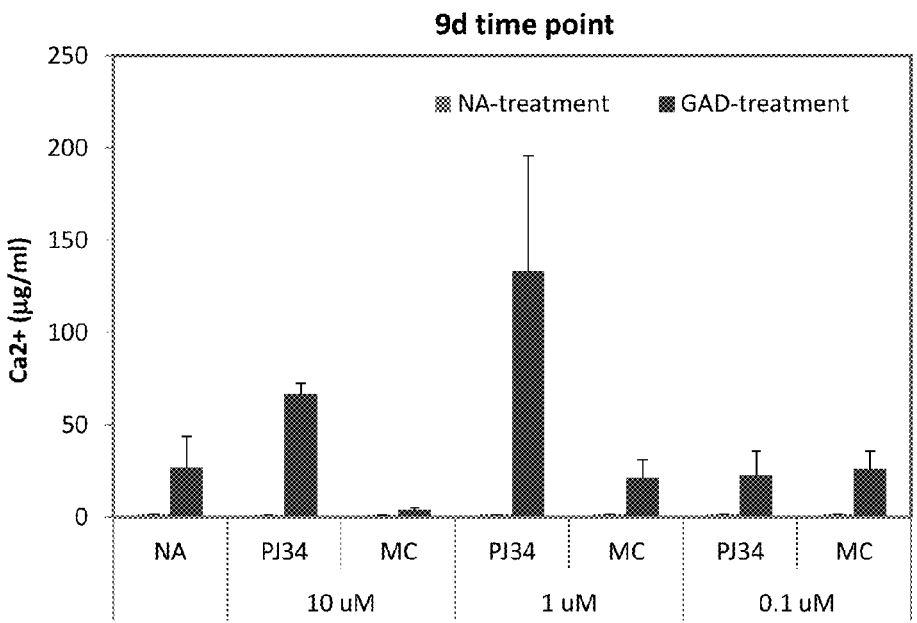
FIG. 13 is a graph showing the $Ca^{2+}$ concentration in a sample of bVSMCs which were incubated for 9 days with control medium (no GAD) or with β-GAD medium (with GAD) in the presence of no potential inhibitors (NA) or in the presence of PJ34 or minocycline (MC) at concentrations of 10 µM, 1 µM or 0.1 µm.
Figure 16:
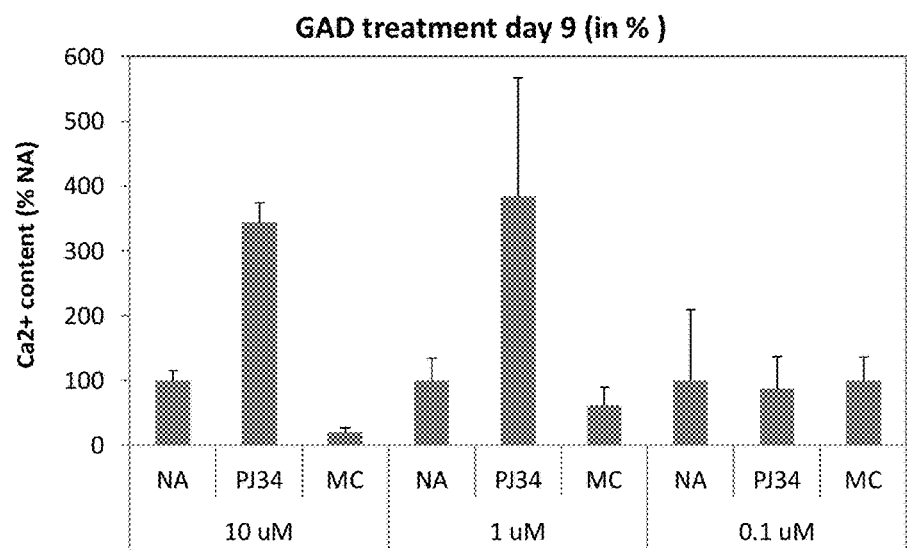
FIG. 16 is a graph showing the $Ca^{2+}$ concentration in a sample of bVSMCs grown in GAD medium over nine days with or without a potential inhibitor expressed as a percentage compared to bVSMCs grown in GAD medium over nine days without a potential inhibitor (NA)

As shown in FIGS. 9B, 13 and 16, minocycline inhibits calcification in a dose dependent manner.

Tetracyclines are a group of broad-spectrum antibiotics having the following structure of formula I:—

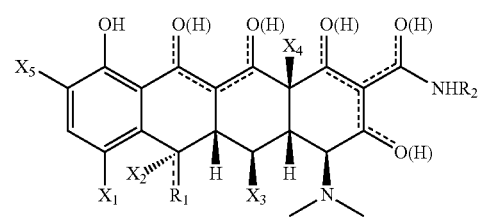

[Formula I]

wherein:
$X_1$ is H, Cl or $N(CH_3)_2$;
$R_1$ is H or $CH_3$ and $X_2$ is H or OH; or $R_1$ is $CH_2$ and $X_1$ is not present;
$X_3$ is OH or H;
$X_4$ is OH;
$R_2$ is H,

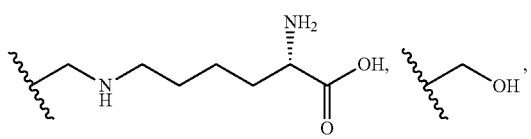

and
$X_5$ is H or

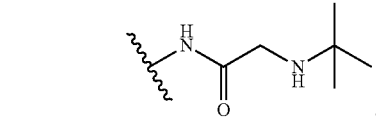

.

Preferably, the tetracycline for use in treating, preventing or ameliorating medial vascular calcification is a compound of formula (I) or a pharmaceutically acceptable salt or solvate thereof.

The tetracycline may be selected from a group consisting of: tetracycline; chlortetracycline; oxytetracycline; demeclocycline; lymecycline; meclocycline; metacycline; minocycline; rolitetracycline; doxycycline; tigecycline; clomocycline; and pipacycline. As shown in FIGS. 9B, 13 and 16, minocycline inhibits calcification in a dose dependent manner. Hence, most preferably the tetracycline is minocycline. It will be appreciated that minocycline is both a PARP inhibitor and also a tetracycline.

Pharmaceutically acceptable salts include any salt of a PARP inhibitor and/or tetracycline provided herein which retains its biological properties and which is not toxic or otherwise undesirable for pharmaceutical use. The pharmaceutically acceptable salt may be derived from a variety of organic and inorganic counter-ions well known in the art.

The pharmaceutically acceptable salt may comprise an acid addition salt formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids. Alternatively, the pharmaceutically acceptable salt may comprise a base addition salt formed when an acidic proton present in the parent compound is either replaced by a metal ion, e.g., an alkali metal ion, an alkaline earth ion, an aluminium ion, alkali metal or alkaline earth metal hydroxides, such as sodium, potassium, calcium, magnesium, aluminium, lithium, zinc, and barium hydroxide, or coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

For instance, a pharmaceutically acceptable salt of pipacycline may be penimepicycline.

A pharmaceutically acceptable solvate refers to a PARP inhibitor and/or tetracycline provided herein, or a salt thereof, that further includes a stoichiometric or non-stoichiometric amount of solvent bound by non-covalent intermolecular forces. Where the solvent is water, the solvate is a hydrate.

It will be appreciated that the PARP inhibitor and/or tetracycline described herein, or a pharmaceutically acceptable salt or solvate thereof, may be used in a medicament which may be used in a monotherapy (i.e. use of the PARP inhibitor and/or tetracycline alone), for treating, ameliorating, or preventing medial vascular calcification or intimal atherosclerotic calcification. Alternatively, PARP inhibitor and/or tetracycline or a pharmaceutically acceptable salt or solvate thereof may be used as an adjunct to, or in combination with, known therapies for treating, ameliorating, or preventing medial vascular calcification or intimal atherosclerotic calcification.

The PARP inhibitor and/or tetracycline may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micellar solution, transdermal patch, liposome suspension or any other suitable form that may be administered to a person or animal in need of treatment. It will be appreciated that the vehicle of medicaments according to the invention should be one which is well-tolerated by the subject to whom it is given.

Medicaments comprising the PARP inhibitor and/or tetracycline described herein may be used in a number of ways. Compositions comprising the PARP inhibitor and/or tetracycline of the invention may be administered by inhalation (e.g. intranasally). Compositions may also be formulated for topical use. For instance, creams or ointments may be applied to the skin.

The PARP and/or tetracycline inhibitor according to the invention may also be incorporated within a slow- or delayed-release device. Such devices may, for example, be inserted on or under the skin, and the medicament may be released over weeks or even months. The device may be located at least adjacent the treatment site. Such devices may be particularly advantageous when long-term treatment with the PARP inhibitor and/or tetracycline used according to the invention is required and which would normally require frequent administration (e.g. at least daily injection).

The PARP inhibitor and/or tetracycline and compositions according to the invention may be administered to a subject by injection into the blood stream or directly into a site requiring treatment, for example a specific blood vessel (vein or artery) which is suffering from calcification. Injections may be intravenous (bolus or infusion) or subcutaneous (bolus or infusion), or intradermal (bolus or infusion).

In a preferred embodiment, the PARP inhibitor and/or tetracycline is administered orally. Accordingly, the PARP inhibitor and/or tetracycline may be contained within a composition that may, for example, be ingested orally in the form of a tablet, capsule or liquid.

It will be appreciated that the amount of the PARP inhibitor and/or tetracycline that is required is determined by its biological activity and bioavailability, which in turn depends on the mode of administration, the physiochemical properties of the PARP inhibitor and/or tetracycline, and whether it is being used as a monotherapy, or in a combined therapy. The frequency of administration will also be influenced by the half-life of the PARP inhibitor and/or tetracycline within the subject being treated. Optimal dosages to be administered may be determined by those skilled in the art, and will vary with the particular PARP inhibitor and/or tetracycline in use, the strength of the pharmaceutical composition, the mode of administration, and the advancement of the medial vascular calcification. Additional factors depending on the particular subject being treated will result in a need to adjust dosages, including subject age, weight, gender, diet, and time of administration.

The PARP inhibitor and/or tetracycline may be administered before, during or after onset of the medial vascular calcification to be treated. Daily doses may be given as a single administration. However, preferably, the PARP inhibitor and/or tetracycline is given two or more times during a day, and most preferably twice a day.

The daily dose of the PARP inhibitor and/or tetracycline to be administered may be between 1 mg and 10000 mg or between 2 mg and 2000 mg, more preferably between 5 mg and 1000 mg or between 10 mg and 200 mg, and most preferably between 15 mg and 100 mg or between 20 mg and 50 mg.

In a most preferred embodiment, the PARP inhibitor and/or tetracycline according to the invention may be administered as two daily doses, each dose being between 1 mg and 5000 mg or between 2 mg and 1000 mg, more preferably between 3 mg and 500 mg or between 4 mg and 100 mg, and most preferably between 5 mg and 50 mg or between 10 mg and 25 mg. A most preferred dosage includes two doses of 10-25 mg.

A patient receiving treatment may take a first dose upon waking and then a second dose in the evening (if on a two dose regime) or at 3- or 4-hourly intervals thereafter. Alternatively, a slow release device may be used to provide optimal doses of the PARP inhibitor and/or tetracycline according to the invention to a patient without the need to administer repeated doses.

Known procedures, such as those conventionally employed by the pharmaceutical industry (e.g. in vivo experimentation, clinical trials, etc.), may be used to form specific formulations comprising the PARP inhibitor and/or tetracycline according to the invention and precise therapeutic regimes (such as daily doses of the PARP inhibitor and/or tetracycline and the frequency of administration). The inventors believe that they are the first to describe a pharmaceutical composition for treating medial vascular calcification, based on the use of the PARP inhibitor and/or tetracycline of the invention.

Hence, in a third aspect of the invention, there is provided a pharmaceutical composition for treating medial vascular calcification or intimal atherosclerotic calcification comprising a PARP inhibitor and/or tetracycline, or a pharmaceutically acceptable salt or solvate thereof, and a pharmaceutically acceptable vehicle.

The pharmaceutical composition can be used in the therapeutic amelioration, prevention or treatment in a subject of medial vascular calcification or intimal atherosclerotic calcification.

The invention also provides, in a fourth aspect, a process for making the composition according to the third aspect, the process comprising contacting a therapeutically effective amount of a PARP inhibitor and/or tetracycline of the first aspect, or a pharmaceutically acceptable salt or solvate thereof, and a pharmaceutically acceptable vehicle.

A "subject" may be a vertebrate, mammal, or domestic animal. Hence, the PARP inhibitor and/or tetracycline, compositions and medicaments according to the invention may be used to treat any mammal, for example livestock (e.g. a horse), pets, or may be used in other veterinary applications. Most preferably, however, the subject is a human being.

A "therapeutically effective amount" of the PARP inhibitor and/or tetracycline is any amount which, when administered to a subject, is the amount of drug that is needed to treat the medial vascular calcification.

For example, the therapeutically effective daily amount of the PARP inhibitor and/or tetracycline used may be between 1 mg and 1000 mg or between 2 mg and 2000 mg, more preferably between 5 mg and 1000 mg or between 10 mg and 200 mg, and most preferably between 15 mg and 100 mg or between 20 mg and 50 mg. Two daily doses of 10-25 mg is preferred.

A "pharmaceutically acceptable vehicle" as referred to herein, is any known compound or combination of known compounds that are known to those skilled in the art to be useful in formulating pharmaceutical compositions.

In one embodiment, the pharmaceutically acceptable vehicle may be a solid, and the composition may be in the form of a powder or tablet. A solid pharmaceutically acceptable vehicle may include one or more substances which may also act as flavouring agents, lubricants, solubilisers, suspending agents, dyes, fillers, glidants, compression aids, inert binders, sweeteners, preservatives, dyes, coatings, or tablet-disintegrating agents. The vehicle may also be an encapsulating material. In powders, the vehicle is a finely divided solid that is in admixture with the finely divided active agents (i.e. PARP inhibitor or the tetracycline) according to the invention. In tablets, the active PARP inhibitor and/or tetracycline may be mixed with a vehicle having the necessary compression properties in suitable proportions and compacted in the shape and size desired. The powders and tablets preferably contain up to 99% of the active PARP inhibitor and/or tetracycline. Suitable solid vehicles include, for example calcium phosphate, magnesium stearate, talc, sugars, lactose, dextrin, starch, gelatin, cellulose, polyvinylpyrrolidine, low melting waxes and ion exchange resins. In another embodiment, the pharmaceutical vehicle may be a gel and the composition may be in the form of a cream or the like.

However, the pharmaceutical vehicle may be a liquid, and the pharmaceutical composition is in the form of a solution. Liquid vehicles are used in preparing solutions, suspensions, emulsions, syrups, elixirs and pressurized compositions. The PARP inhibitor and/or tetracycline according to the invention may be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be a halogenated hydrocarbon or other pharmaceutically acceptable propellant.

Liquid pharmaceutical compositions, which are sterile solutions or suspensions, can be utilized by, for example, intramuscular, intrathecal, epidural, intraperitoneal, intravenous and particularly subcutaneous injection. The PARP inhibitor and/or tetracycline may be prepared as a sterile solid composition that may be dissolved or suspended at the time of administration using sterile water, saline, or other appropriate sterile injectable medium.

The PARP inhibitor and/or tetracycline and compositions of the invention may be administered in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. The PARP inhibitor and/or tetracycline used according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

In accordance with a further aspect of the invention, there is provided a tetracycline and/or a poly(ADP ribose) polymerase (PARP) inhibitor, or a pharmaceutically acceptable salt or solvate thereof, for use in treating, preventing or ameliorating a disease characterised by inappropriate vascular calcification.

According to a still further aspect of the invention, there is provided a method of treating, preventing or ameliorating a disease characterised by inappropriate vascular calcification in a subject, the method comprising administering to a subject in need of such treatment, a therapeutically effective amount of a tetracycline and/or a poly(ADP ribose) polymerase (PARP) inhibitor, or a pharmaceutically acceptable salt or solvate thereof.

According to a still further aspect, there is provided a method of reducing vascular calcification in a subject, the method comprising administering to a subject in need of such treatment, a therapeutically effective amount of a poly(ADP ribose) polymerase (PARP) inhibitor and/or a tetracycline, or a pharmaceutically acceptable salt or solvate thereof.

The vascular calcification may comprise atherosclerotic calcification. Alternatively, the vascular calcification may comprise medial calcification.

All features described herein (including any accompanying claims, abstract and drawings), and/or all of the steps of any method or process so disclosed, may be combined with any of the above aspects in any combination, except combinations where at least some of such features and/or steps are mutually exclusive.

EXAMPLES

The inventors have carried out various experiments which may be summarised like so:

Example 1: Proving the physiological connection between poly(ADP ribose) (PAR) and vascular calcification;

Example 2: Examining the toxicity of PARP inhibitors/tetracyclines to bovine vascular smooth muscle cells;

Example 3: Examining the toxicity of PARP inhibitors/tetracyclines to human monocyte macrophages;

Example 4: Initial tests of PARP inhibitors/tetracyclines on an in-vitro bovine vascular smooth muscle cell vascular calcification model;

Example 5: Dose dependence of trial inhibitors on calcification levels in the in-vitro bovine vascular smooth muscle cell vascular calcification model;

Example 6: Example dose suggestion for trial inhibitors using a pk concentration correlation;

Example 7: Initial tests of PARP inhibitors/tetracyclines on an in-vitro human vascular smooth muscle cell vascular calcification model;

Example 8: Further tests of PARP inhibitors/tetracyclines on an in-vitro human vascular smooth muscle cell vascular calcification model, including olaparib, rucaparib, niraparib, veliparib and talazoparib in the list of compounds tested; and Example 9: Further tests of PARP inhibitors/tetracyclines and other common cardiovascular drugs on an in-vitro human vascular smooth muscle cell vascular calcification model, including losartan, amlodipine and atorvastatin in the list of compounds tested.

Example 1: Proving the Physiological Connection Between Poly(ADP Ribose) (PAR) and Vascular Calcification Vascular smooth muscle cells (VSMCs) calcify their surrounding extracellular matrix when they are under stress. An in vitro model of VSMC tissue was used to determine whether VSMCs under stress produce poly(ADP ribose) (PAR) in any appreciable quantity.

In this model, VSMCs were grown in high concentrations of glucose which induces oxidative stress in the cells. The cells synthesise extracellular matrix and mineralise the matrix, then cell lysis mimicking cell necrosis removes the cells from the matrix. The matrices were washed at least six times with phosphate buffer after cell lysis so that any molecular components not strongly bound to the matrix were removed.

The cell culture medium in these experiments contained U-$^{13}$C-glucose and U-$^{13}$C, $^{15}$N-glycine and proline, so that all sugar species that the cells synthesise from glucose were $^{13}$C-labelled as was collagen (which in composition contains ~33% glycine and 22% proline/hydroxyproline). The collagen and sugar content of the resulting matrices could then be examined by two-dimensional $^{13}$C-$^{13}$C correlation spectra, allowing the detailed characterization of the sugar composition of the matrix with respect to collagen.

Figure 1B:
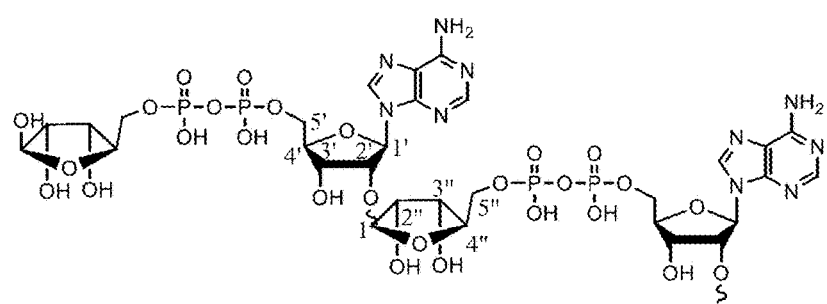
FIG. 1B illustrates the poly(ADP ribose) atom numbering scheme used in FIG. 1A.

FIG. 1 shows a typical two-dimensional $^{13}$C-$^{13}$C correlation spectra obtained from this experiment. All the spectra clearly showed the signals expected for PAR. The fact that $^{13}$C NMR signals are observed from PAR after the matrix was washed indicates strong binding or trapping of the PAR in the matrix.

The inventors then imaged ex vivo human carotid artery lesions for calcification deposits and the presence of PAR and DNA-damage (red is the H2A.X antibody). Mineral deposits were imaged using phase contrast imaging and calcein staining. In adjacent sections, indirect immunohistochemical staining was used to image PAR (using the monoclonal anti poly(ADP ribose) antibody clone 10H, green fluorescence), and DNA damage (using a monoclonal antibody against H2A.X, red fluorescence).

Figure 2:
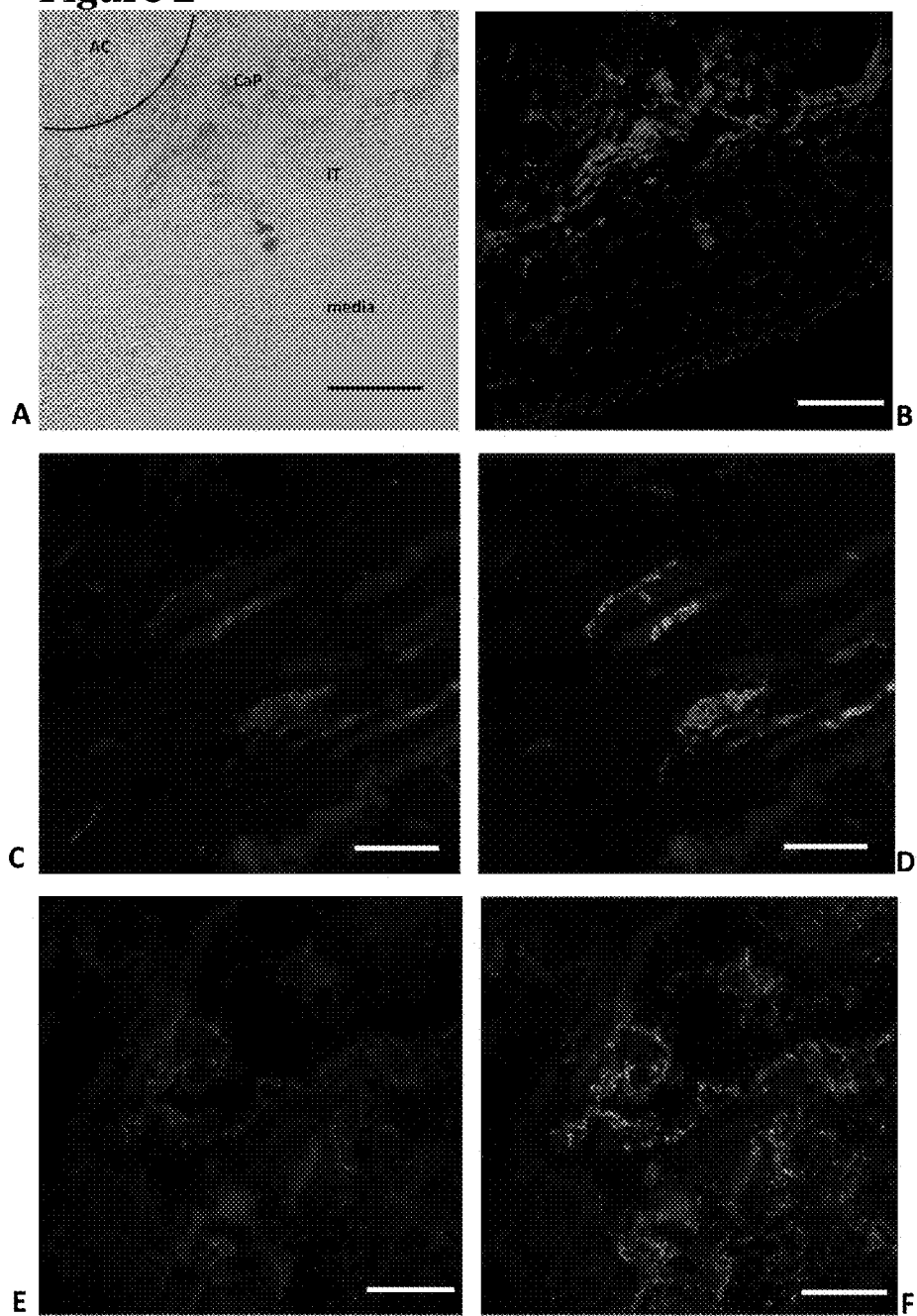
FIG. 2 shows the expression of poly(ADP ribose) (PAR)/ DNA damage in human carotid artery lesions. Phase-contrast (A) and fluorescent image (B) of human carotid lesions at low magnification (scale bar is 150 μm). In the top left of the image is the acellular core (AC) of the lesion, bordered by an area of intimal thickening (iT) with calcification (CaP) next to the media (bottom right). Lesion calcification is clearly visible as a dark deposit in (A) and as green fluorescence after calcein staining in (B). Cell nuclei are stained with Hoechst dye and appear blue. Immunostaining for DNA-damage (γH2AX antibody, red) and PAR (clone 10H antibody, green) in the media (C and D, scale bars are 18 μm) reveals staining located predominantly near the nucleus; in contrast, in the area of intimal thickening/calcification (E and F, scale bars are 16 μm) the staining is more extensive and located in association with the nucleus as well as cytoplasmic and/or extracellular areas.

FIG. 2 shows a phase contrast image and fluorescent imaging from adjacent sections of a lesion. Both the phase contrast image and fluorescence image of the calcein staining clearly show the presence of mineral deposits in a region of intimal thickening in the lesion, adjacent to the necrotic, acellular core of the lesion. In the adjacent section (section thickness 5 μm), there is significant staining for poly(ADP ribose), both in the region of cell nuclei, and cytoplasmic and/or extracellular matrix areas. Similar patterns of poly (ADP ribose) staining are seen in ex vivo coronary artery atherosclerotic lesions.

A key question was what drives the synthesis of poly (ADP ribose) in developing bone and in oxidatively stressed vascular tissue. Poly(ADP ribose) has well-documented roles in cell death (apoptosis via mitochondrial release of AIF or parthanatos when DNA damage drives excessive PARP expression causing impairment of glycolysis) and in DNA repair. In terms of cell death associated with matrix calcification, 60-80% of osteoblasts die during bone calcification. Similarly, cell death (apoptosis and necrosis) always precedes vascular calcification whether the calcification is associated with atherosclerosis or medial calcification. The possibility for DNA damage to be associated with vascular calcification is strong: DNA damage in oxidatively stressed vascular smooth muscle cells from reactive oxygen/nitrogen species is a likely scenario. Perhaps less intuitively and therefore even more interesting, SAOS-2 cells, an osteoblastic cell line, release hydrogen peroxide when they express osteogenic markers and the hydrogen peroxide release goes hand-in-hand with poly(ADP ribose) synthesis, suggesting a possible DNA-damage dependent mechanism of poly(ADP ribose) synthesis in bone development too.

Thus, the inventors hypothesized that the appearance of poly(ADP ribose) in the extracellular matrix may be from DNA damage-dependent cell death and so they examined both developing bone and human vascular calcification deposits for the presence of DNA damage in cells spatially associated within calcifying regions. FIG. 2 (right hand column) shows that in vascular calcification, both nuclear and extracellular poly(ADP ribose) staining co-localizes with phosphorylated histone, H2A.X, a marker of DNA damage.

Figure 3:
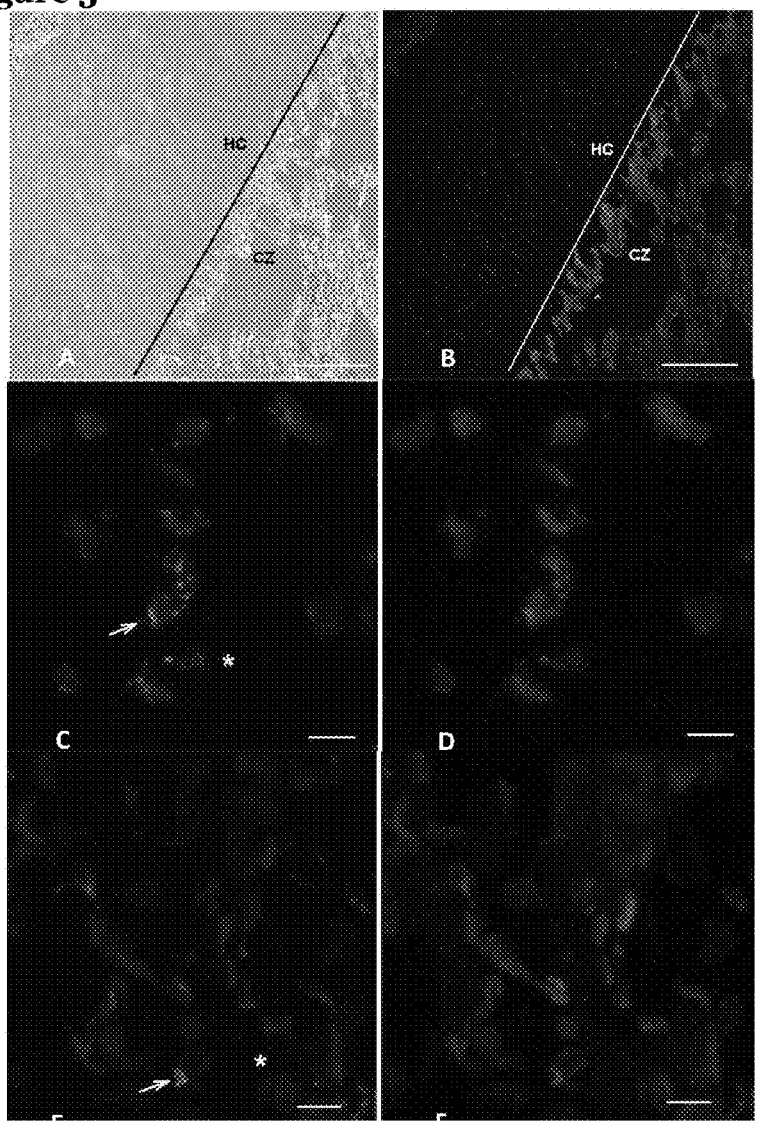
FIG. 3 shows the expression of poly(ADP ribose) (PAR)/ DNA damage in foetal sheep bone growth plate. Phase-contrast (A) and fluorescent image (B) of foetal sheep growth plate at low magnification (scale bar is 150 μm). In the top left of the image is the zone of hypertrophic cartilage (HC) of the growth plate, bordering onto the calcification zone (CF), where mineral starts to form (bottom right). Mineral is clearly visible by the green fluorescence after calcein staining in (B). Cell nuclei are stained with Hoechst dye and appear blue. Immunostaining for PAR (clone 10H antibody, green) and DNA-damage (H2A.X antibody, red) in the HC zone near the border where mineralization occurs (C and D, scale bars are 10 μm) reveals predominantly staining located near the nucleus (arrow), but weak staining is visible also away from nuclear DNA (asterisk). In the CF zone surrounding the bone trabeculae (E and F, scale bars are 10 um) PAR and DNA-damage stainings are located in association with the nucleus (arrow) as well as cytoplasmic and/or extracellular areas (asterisk)

FIG. 3 shows a very similar relationship between poly (ADP ribose) and H2A.X in foetal bone growth plate—co-localization of poly(ADP ribose) and H2A.X in both cell nuclei and the extracellular matrix.

The direct association of poly(ADP ribose) with bone and vascular mineral deposits suggests a mechanistic link between the extracellular deposition of poly(ADP ribose) and the induction of mineral formation.

Example 2: Toxicity of Poly(ADP Ribose) Polymerase (PARP) Inhibitors Over Seven Days to Bovine Vascular Smooth Muscle Cells (bVSMCs)

Given the mechanistic link between the extracellular deposition of PAR and the induction of mineral formation, it was decided to test PARP inhibitors to see if they would inhibit vascular calcification.

PJ34, minocycline (MC) and 3-AB have been shown to inhibit PARP produced by a mammalian cell. Accordingly, these compounds were identified to be tested.

Additionally cilostazol (CS), bosentan MH (Bos MH), pentoxifylline (PF), diltiazem (DZ) and dipyridamol (DP) have all been shown to inhibit recombinant PARP. Accordingly, while it is not known for sure if these compounds are true PARP inhibitors, it was decided that they should also be tested.

The toxicity of the identified compounds to bovine VSMCs was measured using the MTT assay, which measures the activity of dehydrogenase enzymes of live cells. This assay can pick up both cell death and proliferation.

Methodology

Bovine VSMCs were seeded in 96 well plates and cultured in M199/20% FCS for 1 day. Then, the cells were incubated with inhibitor concentrations from 0.5 to 100 μM (in M199 medium+5% FBS). The cells were incubated with the inhibitors for 7 days; every 2-3 days the medium −/+inhibitors was exchanged. Then, the MTT assay was performed. The stock vehicle DMSO was tested at corresponding concentrations to the inhibitors at 0.1% DMSO or less.

Results

Figure 4A:
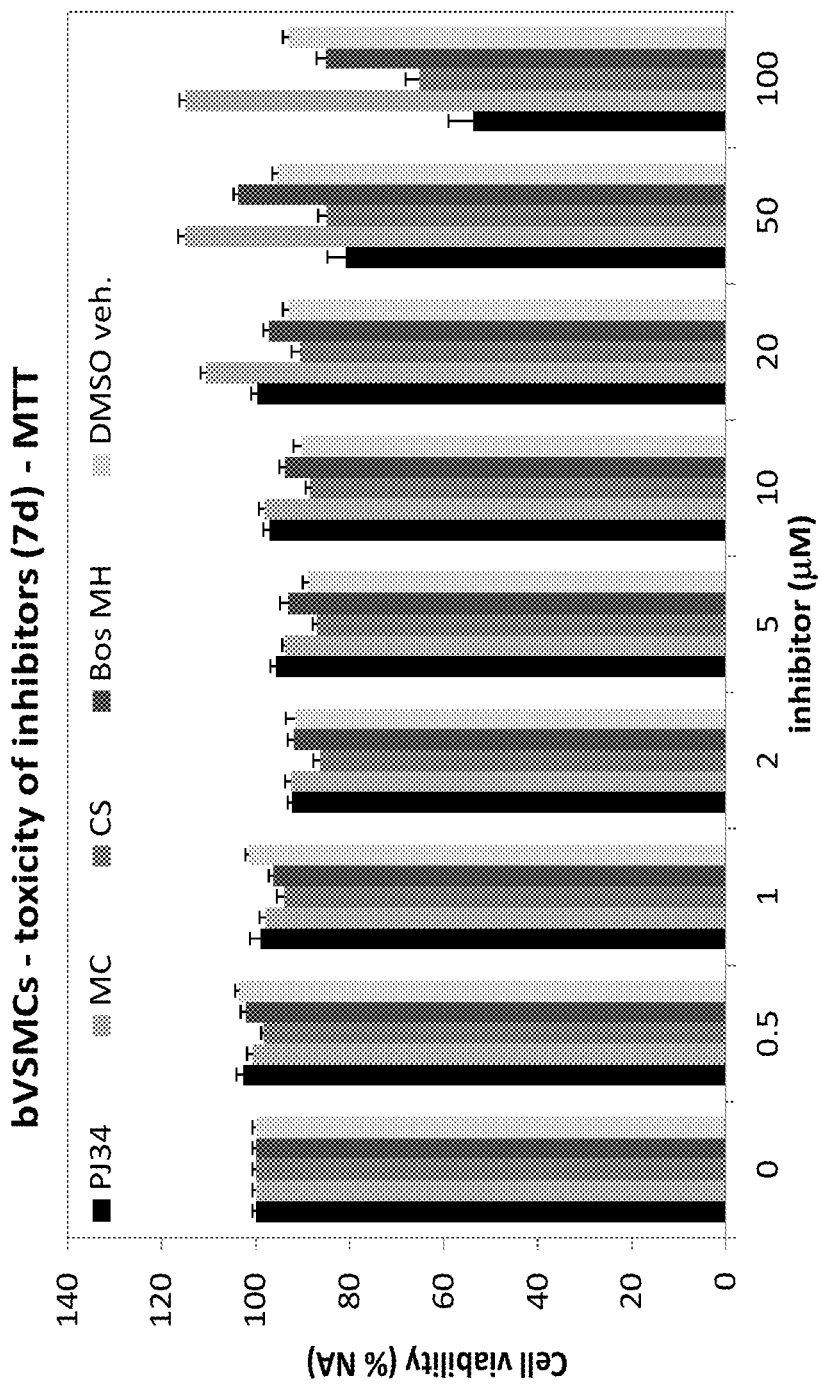
FIGS. 4A and 4B are graphs showing the toxicity of N-(6-Oxo-5,6-dihydrophenanthridin-2-yl)-(N,N-dimethylamino)acetamide hydrochloride (PJ34), minocycline (MC), cilostazol (CS), bosentan MH (Bos MH), pentoxifylline (PF), diltiazem (DZ), dipyridamol (DP), 3-aminobenzamide (3-AB) and 3,4-dihydro-5-[4-(1-piperidinyl)butoxyl]-1 (2H)-isoquinolinone (DPQ) at concentrations from 0 to 100 μM, and the DMSO vehicle at the corresponding dilutions, over seven days to bovine vascular smooth muscle cells (bVSMCs)
Figure 4B:
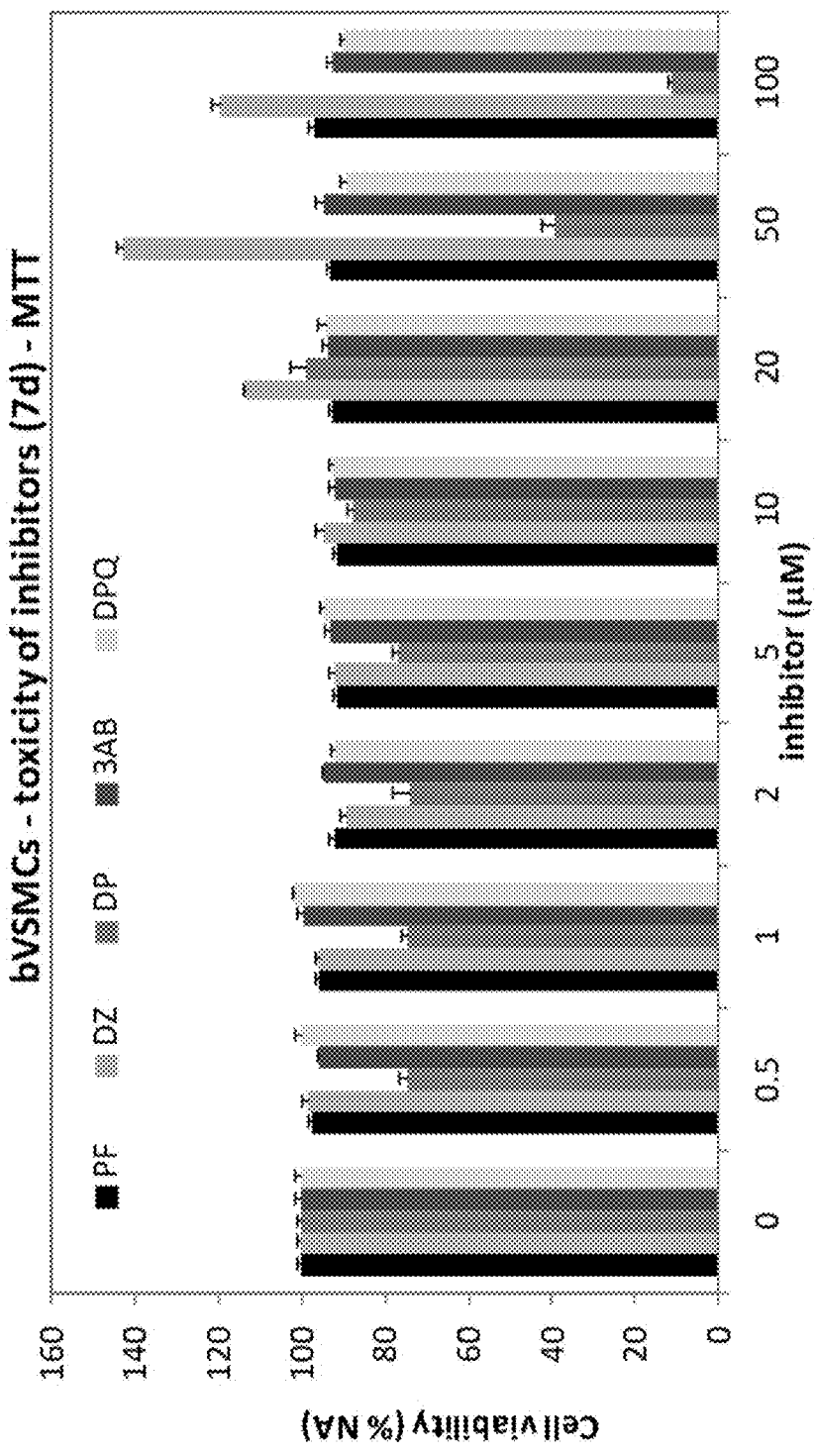

The results are given in Table 1, below, and shown graphically in FIG. 4. The values given represent the mean of three experiments, each in duplicate. In FIG. 4, error bars represent the standard error (SE) of the three experiments. Values marked with an asterisk (*) in the table below are deemed statistically significant compared to the NA control (no inhibitor); $p \geq 0.01$ (ANOVA+post-hoc LSD test).

TABLE 1

Toxicity of potential inhibitors over seven days to bVSMCs

| | PJ34 | | minocycline | | cilostazol | | bosentan MH | | DMSO | | |
|---|---|---|---|---|---|---|---|---|---|---|---|
| uM | Mean | SE | Mean | SE | Mean | SE | Mean | SE | Mean | SE | % |
| 0 | 100.00 | 0.62 | 100.00 | 0.62 | 100.00 | 0.62 | 100.00 | 0.62 | 100.00 | 0.62 | 0 |
| 0.5 | 102.59 | 1.55 | 100.61 | 1.30 | 98.22 | 0.64 | 101.97 | 1.31 | 103.56 | 0.87 | 0.0005 |
| 1 | 98.89 | 2.43 | 97.88 | 1.36 | 93.93 | 1.68 | 96.12 | 1.06 | 101.40 | 0.72 | 0.001 |
| 2 | 92.33 | 0.91 | 92.51* | 1.35* | 86.31* | 1.45* | 91.91* | 1.25* | 91.69* | 1.98* | 0.002 |
| 5 | 95.74 | 1.27 | 93.80* | 0.66* | 86.87* | 1.03* | 93.05* | 1.73* | 88.79* | 1.31* | 0.005 |
| 10 | 97.07 | 1.38 | 98.08 | 1.20 | 88.38* | 1.07* | 93.87* | 1.07* | 90.18* | 1.81* | 0.01 |
| 20 | 99.71 | 1.32 | 110.52* | 1.27* | 90.45* | 2.00* | 97.20 | 1.20 | 92.85* | 1.45* | 0.02 |
| 50 | 80.83* | 4.03* | 115.14* | 1.39* | 84.93* | 1.90* | 103.69 | 1.05 | 95.37 | 1.06 | 0.05 |
| 100 | 53.72* | 5.33* | 114.88* | 1.40* | 65.21* | 2.95* | 85.05* | 2.03* | 92.85* | 1.41* | 0.1 |

| | Pentoxifylline | | Diltiazem | | Dipyridamol | | 3-AB | | DPQ | |
|---|---|---|---|---|---|---|---|---|---|---|
| uM | Mean | SE | Mean | SE | Mean | SE | Mean | SE | Mean | SE |
| 0 | 100.00 | 1.17 | 100.00 | 1.17 | 100.00 | 1.17 | 100.00 | 1.96 | 100.00 | 1.96 |
| 0.5 | 97.68 | 1.10 | 98.78 | 1.17 | 74.66* | 2.08* | 95.77 | 0.79 | 100.30 | 1.76 |
| 1 | 95.91 | 1.04 | 96.07 | 0.95 | 74.62* | 1.53* | 99.58 | 1.55 | 101.78 | 0.64 |
| 2 | 92.19* | 1.57* | 89.48* | 1.53* | 74.09* | 4.13* | 94.53 | 0.76 | 92.11* | 0.95* |
| 5 | 91.33* | 1.13* | 91.88* | 2.05* | 76.71* | 1.88* | 93.35* | 1.53* | 94.96 | 0.86 |
| 10 | 91.77* | 0.82* | 94.54 | 2.17 | 87.97* | 1.55* | 91.99* | 1.87* | 92.58* | 1.02* |
| 20 | 92.43* | 0.99* | 113.60* | 0.96* | 99.34 | 3.79 | 93.42* | 1.84* | 94.24* | 2.37* |
| 50 | 93.01* | 0.97* | 143.28* | 1.75* | 39.52* | 2.97* | 94.64 | 2.41 | 89.46* | 1.59* |
| 100 | 96.96 | 1.49 | 119.64* | 2.23* | 11.34* | 0.81* | 92.48* | 1.73* | 89.87* | 1.04* |

The results of the MTT assay show that Pentoxifylline (PF), 3AB, DPQ and the DMSO vehicle are virtually non-toxic at the concentrations tested; Bosentan monohydrate (Bos) also shows little toxicity. PJ34, Dipyridamol (DP) and Cilostazol (CS) are toxic at 50 and 100 µM. Minocycline (MC) and Diltiazem are both non-toxic and in addition show a stimulatory effect on the cells at 20 µM and above. Therefore, all the inhibitors are well tolerated by the bVSMCs at concentrations likely to be used in a calcification model.

Example 3: Toxicity of Potential Inhibitors to Human Monocyte-Macrophages (HMMs)

A similar set of toxicity experiments was performed with human monocyte-macrophages (HMMs). As HMMs do not proliferate in culture, a comparison between dividing cells (bVSMC) and non-dividing cells (HMMs) can sometimes help to distinguish between effects due to toxicity and effects due to proliferation. Moreover, for the intended use of the compounds, it is important to establish that they are not toxic to human macrophages.

The methodology was as described for example 2 except that the HMMs were cultured in Mø-SFM medium (serum-free medium) for routine culture as well as for the toxicity assay.

Results

Figure 5A:
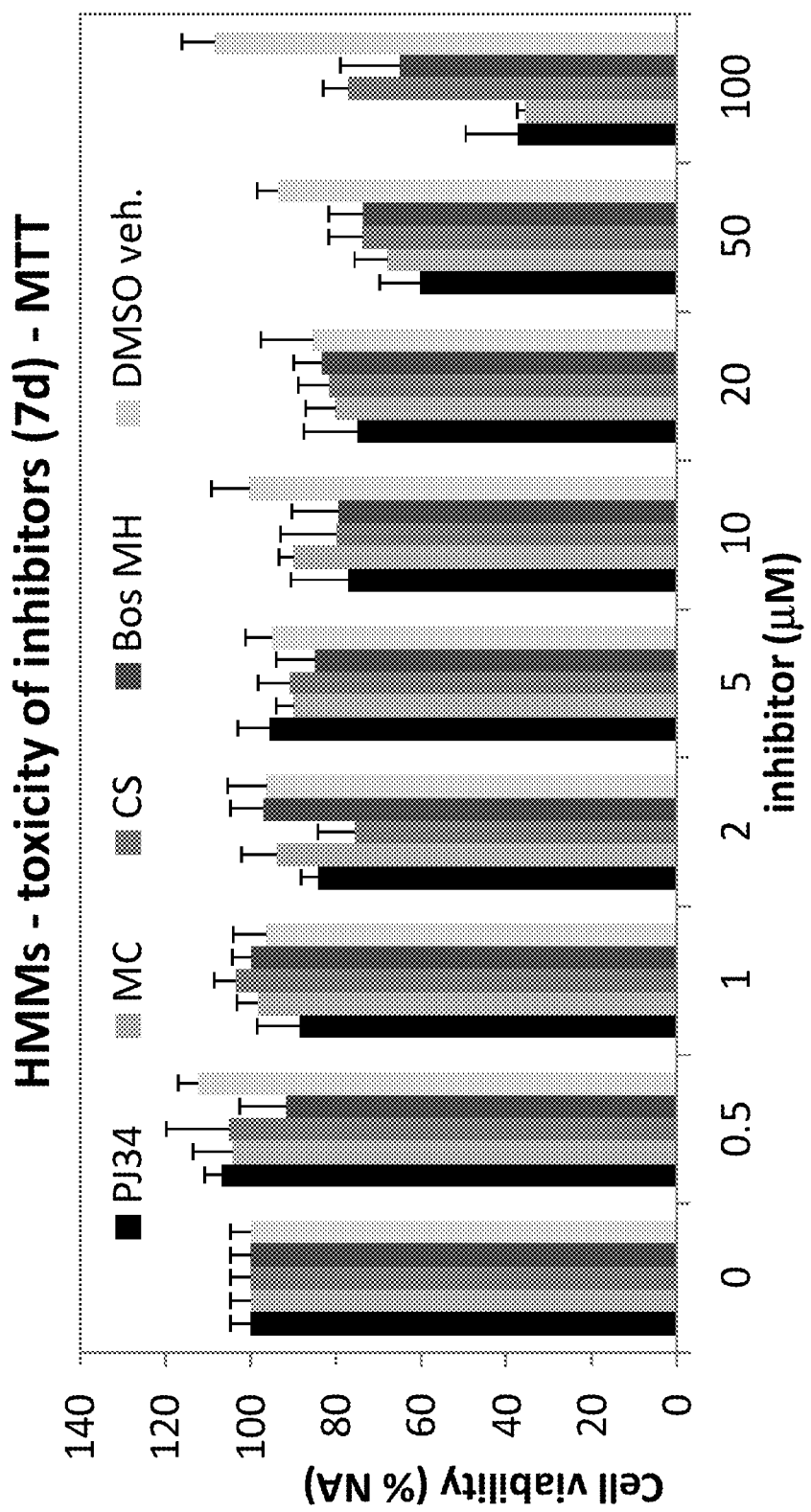
FIGS. 5A and 5B are graphs showing the toxicity of PJ34, minocycline (MC), cilostazol (CS), bosentan MH (Bos MH), pentoxifylline (PF), diltiazem (DZ), dipyridamol (DP), 3-AB and DPQ at concentrations from 0 to 100 μM, and the DMSO vehicle at the corresponding dilutions, over seven days to human monocyte-macrophages (HMMs)
Figure 5B:
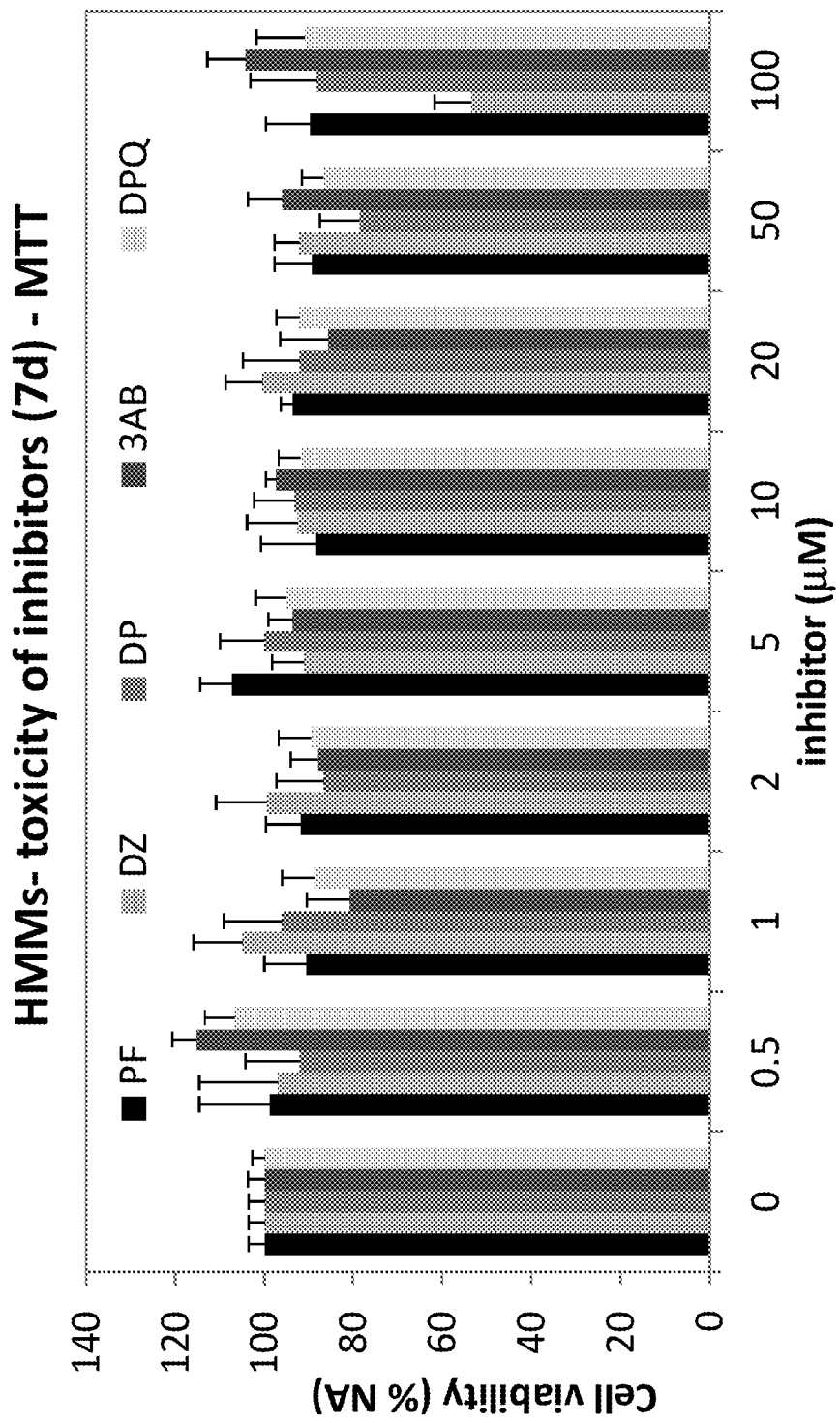

The results are given in Table 2, below, and shown graphically in FIG. 5. As before, the values given represent the mean of three experiments, each in duplicate. In FIG. 5, error bars represent the standard error (SE) of the three experiments. Values marked with an asterisk (*) in the table below are deemed statistically significant compared to the NA control (no inhibitor); p 0.01 (ANOVA+post-hoc LSD test).

The results from Examples 2 and 3 allow us to judge the toxicity of the concentrations of the compounds required to inhibit vascular calcification in the subsequent examples.

Example 4: Initial Test on of Vascular Calcification by PJ34, Minocycline (MC), Cilostazol (CS), Bosentan MH (Bos), 3-AB, Pentoxifylline (PF), Diltiazem (DZ) and Dipyridamol (DP)

Methodology

For the bVSMCs a GAD medium (10 mM β-glycerophosphate/0.1 mM L-ascorbic acid-2-phosphate/10 nM dexamethasone) model was used to induce mineralization in bVSMCs. Accordingly, cells were seeded in tissue culture plates using M199/20% FCS culture medium and cultured overnight. The next day, cells were treated either with medium only (M199/5% FBS)+/−inhibitors, or with the GAD-medium (10 mM β-glycerophosphate/0.1 mM L-ascorbic acid-2-phosphate/m nM dexamethasone)+/−inhibitors.

All the inhibitors were used at a concentration of 10 µM, as examples 2 and 3 show that all of the compounds were non-toxic at this concentration and moreover, did not appear to induce other effects such as significant proliferation which might complicate the assessment of any calcification inhibitory effect they may show. Medium+/−inhibitors was exchanged every 2-3 days. Bovine VSMCs were incubated for 7 d prior to assessment.

Alizarin Red S Staining

The Alizarin Red S staining is a visual/histological stain for tissue calcium deposits. Cells are briefly fixed in 4% paraformaldehyde/PIPES buffer pH 7.2 and subsequently stained for 5 min with Alizarin Red S (2% Alizarin Red S/DIW pH 4.2). Excess stain is removed by washing in DIW. Calcium mineral deposits are stained a bright orange red.

TABLE 2

Toxicity of potential inhibitors over seven days to HMMs

| | PJ34 | | minocycline | | cilostazol | | bosentan MH | | DMSO | | |
|---|---|---|---|---|---|---|---|---|---|---|---|
| uM | Mean | SE | Mean | SE | Mean | SE | Mean | SE | Mean | SE | % |
| 0 | 100.00 | 4.88 | 100.00 | 4.88 | 100.00 | 4.88 | 100.00 | 4.88 | 100.00 | 4.88 | 0 |
| 0.5 | 106.63 | 4.23 | 104.23 | 9.35 | 105.05 | 14.87 | 91.59 | 11.16 | 112.34 | 4.65 | 0.0005 |
| 1 | 88.38 | 10.15 | 98.27 | 5.14 | 103.62 | 4.88 | 99.82 | 4.57 | 96.40 | 7.88 | 0.001 |
| 2 | 84.08 | 4.26 | 94.01 | 8.33 | 75.63 | 8.72 | 97.16 | 7.71 | 96.32 | 9.23 | 0.002 |
| 5 | 95.65 | 7.61 | 89.95 | 4.16 | 90.74 | 7.63 | 84.90 | 9.33 | 94.92 | 6.24 | 0.005 |
| 10 | 77.14 | 13.49 | 89.89 | 3.61 | 79.83 | 13.16 | 79.36 | 11.02 | 100.13 | 9.20 | 0.01 |
| 20 | 74.86 | 12.70 | 80.11 | 7.02 | 81.50 | 7.32 | 83.25 | 6.61 | 85.31 | 12.35 | 0.02 |
| 50 | 60.33* | 9.46* | 67.96* | 7.74* | 73.73 | 7.99 | 73.65 | 8.18 | 93.63 | 4.86 | 0.05 |
| 100 | 37.30* | 12.33* | 35.69* | 1.82* | 77.06 | 5.90 | 64.97* | 14.13* | 108.48 | 7.60 | 0.1 |

| | Pentoxifylline | | Diltiazem | | Dipyridamol | | 3-AB | | DPQ | |
|---|---|---|---|---|---|---|---|---|---|---|
| uM | Mean | SE | Mean | SE | Mean | SE | Mean | SE | Mean | SE |
| 0 | 100.00 | 3.61 | 100.00 | 3.61 | 100.00 | 3.61 | 100.00 | 3.75 | 100.00 | 2.71 |
| 0.5 | 98.73 | 15.98 | 97.10 | 17.55 | 92.12 | 12.25 | 115.25 | 5.50 | 106.61 | 6.70 |
| 1 | 90.57 | 9.55 | 104.94 | 11.10 | 96.12 | 13.00 | 80.78 | 9.67 | 88.68 | 7.38 |
| 2 | 91.92 | 7.76 | 99.61 | 11.36 | 86.73 | 10.65 | 88.03 | 6.08 | 89.59 | 7.28 |
| 5 | 107.27 | 7.17 | 91.09 | 7.27 | 100.16 | 9.79 | 93.51 | 5.55 | 95.11 | 6.84 |
| 10 | 88.35 | 12.44 | 92.45 | 11.50 | 93.21 | 9.22 | 97.34 | 2.34 | 91.82 | 4.92 |
| 20 | 93.54 | 2.78 | 100.42 | 8.26 | 91.98 | 12.88 | 85.76 | 10.59 | 91.99 | 5.45 |
| 50 | 89.28 | 8.49 | 92.16 | 5.59 | 78.60 | 8.94 | 95.92 | 7.91 | 86.74 | 4.94 |
| 100 | 89.64 | 10.08 | 53.65* | 8.26* | 88.21 | 15.05 | 104.20 | 8.55 | 90.94 | 10.88 |

The result of the toxicity assay shows that at a concentration of 100 µM MC, PJ34, DZ and BOS are the most toxic of the inhibitors to HMMs, whereas CS, DP, PF, DPQ and 3AB are relatively innocuous.

o-Cresolphthalein Assay

The o-Cresolphthalein assay is a spectrophotometric method for measuring $Ca^{2+}$-concentrations in cell/tissue lysates. Following the calcification experiments, cells are briefly washed to remove medium and 100 μl of 0.1 N HCl is added to each well to dissolve any mineral deposits. Then, the $Ca^{2+}$-concentration of the samples is measured spectrophotometrically (at 570 nm) in the o-cresolphthalein assay with the help of a $CaCl_2$ standard curve in a concentration range of ~0.02-270 μg $Ca^{2+}$/ml.

BioRad Protein Assay

The commercial BioRad DC protein assay is based on the Lowry method, aka reaction of proteins with a copper-tartrate complex and subsequent reaction with Folin's reagent. Following the calcification experiment, cells are briefly washed to remove medium and 100 μl of solubilisation solution (0.1 M NaOH/1% SDS/DIW) is added to each well to lyse the cells. The protein concentrations of the lysates are subsequently determined in the BioRad DC assay as per supplier's instructions using BSA (bovine serum albumin) as standard.

Results

Figure 6:
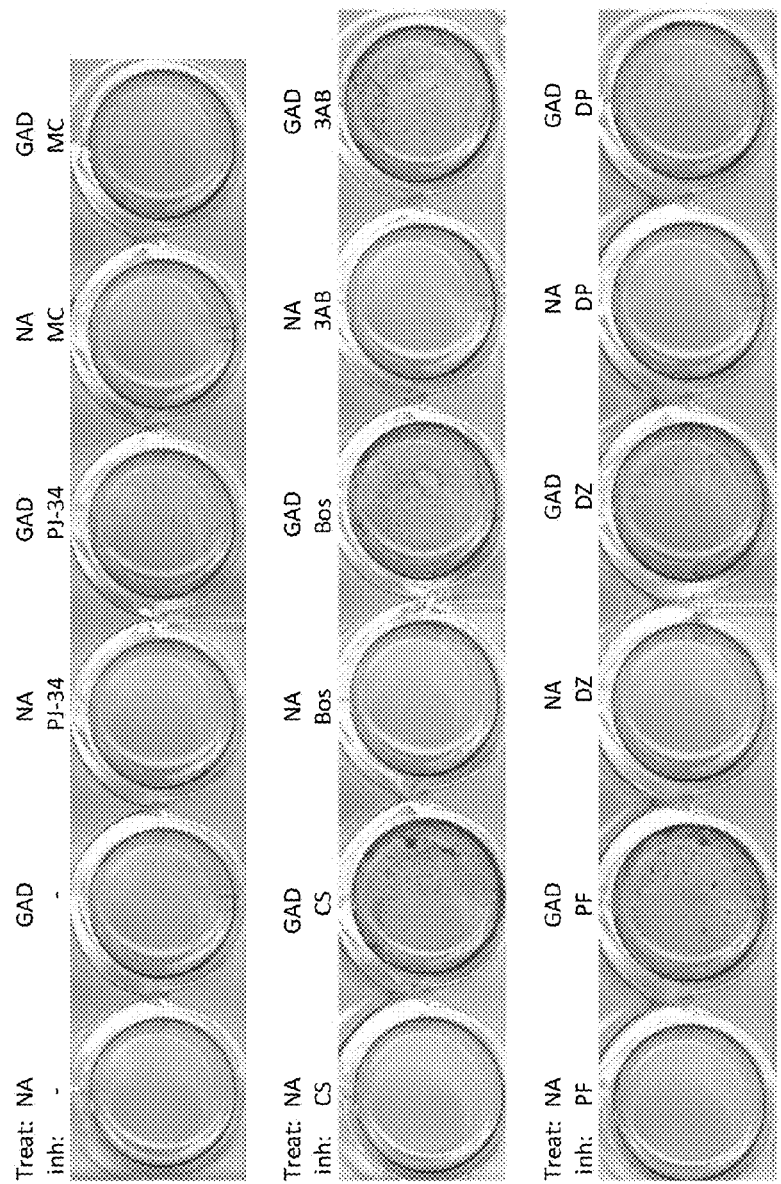
FIG. 6 shows the results obtained using Alizarin Red S staining where bVSMCs were grown with medium only (NA) or in a GAD medium and either no inhibitors were added or PJ34, minocycline (MC), cilostazol (CS), bosentan MH (Bos MH), pentoxifylline (PF), diltiazem (DZ), dipyridamol (DP) or 3-AB were added at a concentration of 10 μM.

A photograph of the plates treated with Alizarin Red S staining is shown in FIG. 6. It is clear that for the cells treated with medium only (NA) no red staining due to Alizarin was visible. This indicates that little or no calcification of the cultures had taken place.

In contrast, the GAD-treated cells stained positive with Alizarin showing calcification of the cultures. Judging by eye, the degree of mineralization was slightly less in the minocycline (MC) sample, and slightly worse in the PJ34 and Dipyridamol (DP) samples.

Figure 7A:
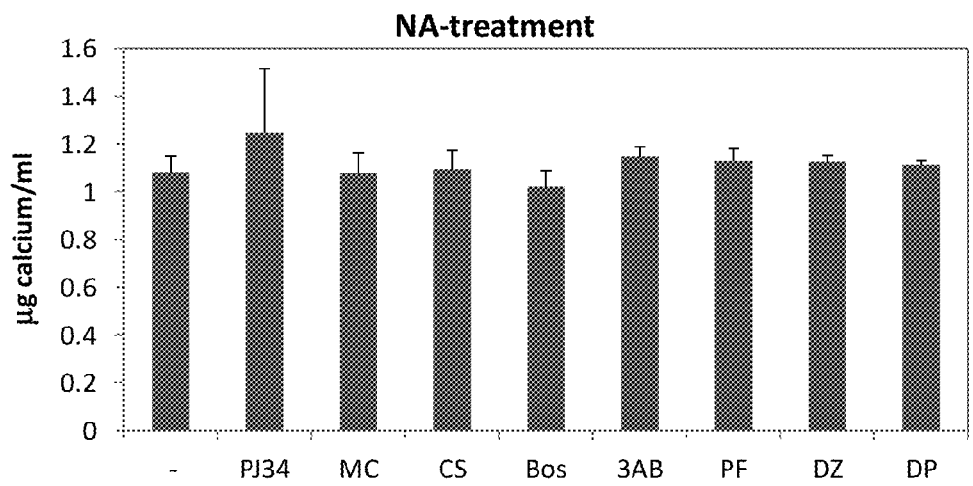
FIG. 7A is a graph showing the mass of calcium obtained from plates where bVSMCs were grown with medium only (NA) and either no inhibitors were added or PJ34, minocycline (MC), cilostazol (CS), bosentan MH (Bos MH), pentoxifylline (PF), diltiazem (DZ), dipyridamol (DP) or 3-AB were added at a concentration of 10 μM.
Figure 7B:
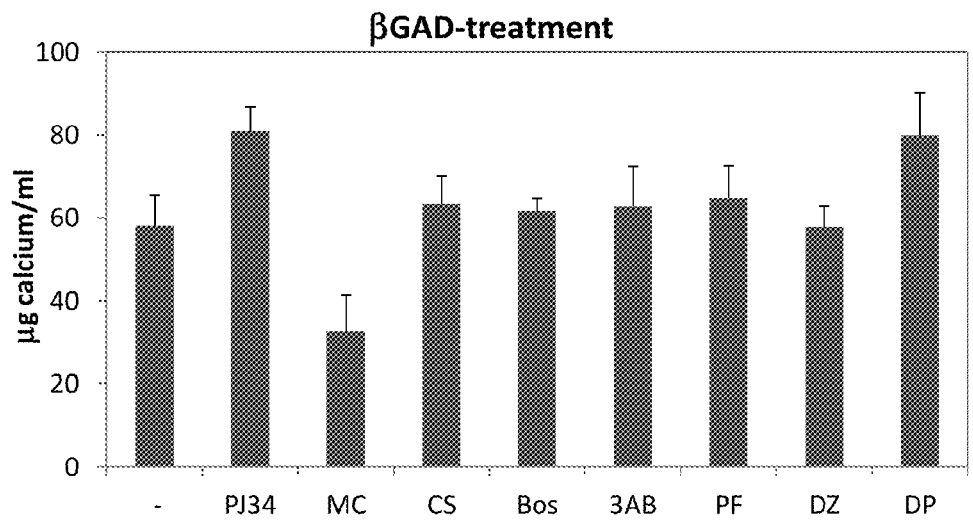
FIG. 7B is a graph showing the mass of calcium obtained from plates where bVSMCs were grown in a GAD medium and either no inhibitors were added or PJ34, minocycline (MC), cilostazol (CS), bosentan MH (Bos MH), pentoxifylline (PF), diltiazem (DZ), dipyridamol (DP) or 3-AB were added at a concentration of 10 μM.

The o-Cresolphthalein assay enabled the inventors to quantify the $Ca^{2+}$ deposition, as shown in FIGS. 7A and 7B.

As shown in FIG. 7A, the cresolphthalein assay showed that the calcium content in the NA-treatment group was very low (basically at the detection limit of the assay). In the GAD-treatment group, shown in FIG. 7B, the calcium levels are elevated to about 50-60 times that of the untreated cells.

As shown in FIG. 7B CS, Bos, 3AB and PF appeared to have no effect on calcium levels, whereas PJ34 and DP appeared to elevate calcium levels. However, DZ and particularly MC appeared to lower calcium levels compared to the samples in which no inhibitors were added.

Figure 8:
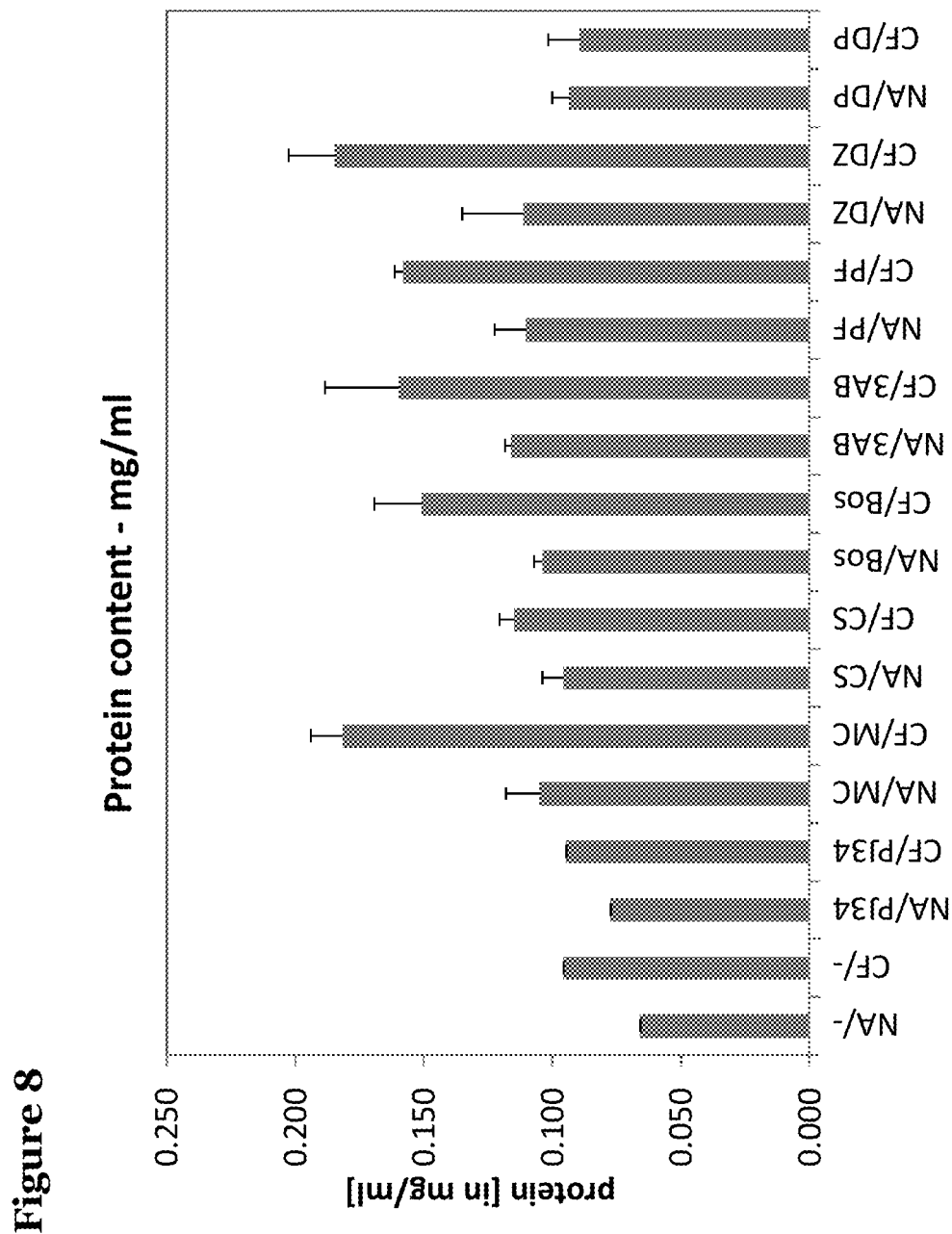
FIG. 8 is a graph showing the protein content for each of the plates where calcium content was given in FIG. 7.

The results of the BioRad protein assay are shown in FIG. 8. When assessing the degree to which a compound inhibits calcification, it is usual to quantify the degree of inhibition as the mass of calcium in the sample (determined by the cresolphthalein assay) per mass of protein in the sample (determined by the BioRad protein assay).

This is because the total mass of protein in the sample may increase during the time period over which the experiment is run, in this case 7 days, because of cell growth, proliferation, or cell synthesis of matrix induced by the added compound. These normalised results are shown in FIG. 9.

As shown in FIG. 9B, when the results are normalised CS still does not appear to have an effect on calcium levels and PJ34 and DP still appeared to elevate calcium levels. However, Bos, 3AB, PF and DZ all appear to slightly lower calcium levels, and MC appears to significantly lower calcium levels.

Example 5: Dose Dependence of Trial Inhibitors on Calcification in the In Vitro Vascular Calcification Model Methodology The in vitro model is the same as the model used in example 4; bovine vascular smooth muscle cells (bVSMCs) cultured so that they produce extracellular matrix, with the addition of the GAD medium (10 mM β-glycerophosphate/0.1 mM L-ascorbic acid-2-phosphate/10 nM dexamethasone).

As above, cells were treated either with medium only ("no-additions"; NA)+/−inhibitors, or with the GAD-medium+/−inhibitors. The inhibitors used were PJ34 and minocyclin (MC) at 10 μM, 1 μM and 0.1 μM. The cell cultures were visually inspected for mineralization and the degree of calcification assessed at 7 days GAD-treatment as this had been planned previously as the first data point. The second time point where the degree of calcification was assessed was taken as 9 days as mineralization in the GAD-treated cells appeared to progress fairly rapidly. Longer treatment duration was deemed risky as the cells have the tendency to peel off the wells and can then be lost altogether.

Similar to example 4, an o-Cresolphthalein assay for quantification of $Ca^{2+}$ deposition and a BioRad protein assay for protein content were carried out. The methodology was the same as that described in example 4.

Additionally, an MTT assay was performed as a measure of cell viability/proliferation. Bovine VSMCs were seeded in 96 well plates and cultured in M199/20% FCS for 1 day. Then, the cells were incubated with inhibitor concentrations of 10 μM, 1 μM and 0.1 μM (in M199 medium+5% FBS). The cells were incubated with the inhibitors for 7 or 9 days; every 2-3 days the medium −/+inhibitors was exchanged. Then, the MTT assay was performed.

Results

MTT Cell Viability Assay

Figure 10:
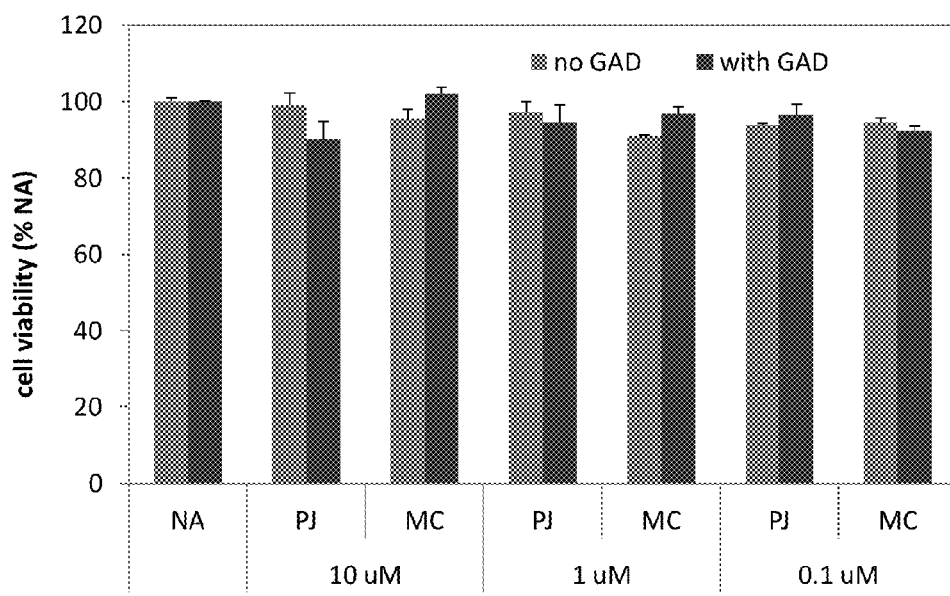
FIG. 10 is a graph showing cell viability results of bVSMCs which were incubated for 7 days with control medium (no GAD) or with β-GAD medium (with GAD) in the presence of no potential inhibitors (NA) or in the presence of PJ34 (PJ) or minocycline (MC) at concentrations of 10 μM, 1 μM or 0.1 μM.
Figure 11:
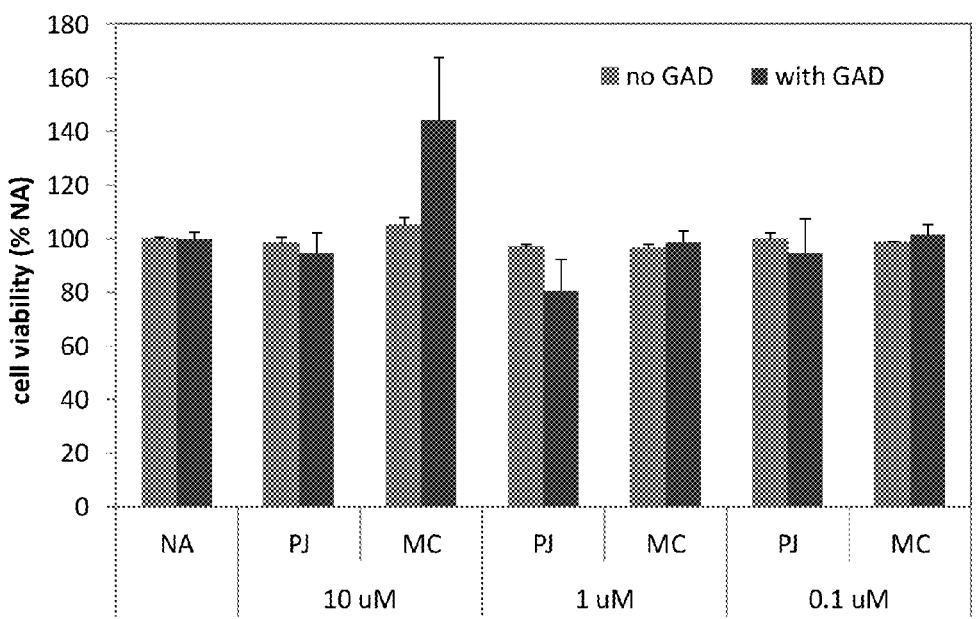
FIG. 11 is a graph cell showing cell viability results of bVSMCs which were incubated for 9 days with control medium (no GAD) or with β-GAD medium (with GAD) in the presence of no potential inhibitors (NA) or in the presence of PJ34 (PJ) or minocycline (MC) at concentrations of 10 μM, 1 μM or 0.1 μM.

The cell viability results for the bVSMCs which were incubated for 7 days are given in Table 3, below, and shown graphically in FIG. 10. Similarly, the cell viability results for the bVSMCs which were incubated for 9 days are given in Table 4, below, and shown graphically in FIG. 11. In each case, the values given represent the mean of three experiments. In FIGS. 10 and 11, error bars represent the standard deviation (SD) of the three experiments.

TABLE 3

Toxicity of medium only and GAD medium in combination with potential inhibitors over seven days to bVSMCs

| Concentration | Potential inhibitor | Cell viability (%) | | | |
|---|---|---|---|---|---|
| | | no GAD | | with GAD | |
| | | mean | SD | mean | SD |
| — | NA | 100 | 1.08 | 100 | 0.16 |
| 10 μM | PJ | 99.25 | 3.12 | 90.03 | 4.83 |
| | MC | 95.49 | 2.45 | 102.07 | 1.79 |
| 1 μM | PJ | 97.16 | 2.92 | 94.61 | 4.71 |
| | MC | 91.09 | 0.4 | 96.84 | 1.8 |
| 0.1 μM | PJ | 93.81 | 0.56 | 96.46 | 2.98 |
| | MC | 94.56 | 1.26 | 92.48 | 1.14 |

TABLE 4

Toxicity of medium only and GAD medium in combination with potential inhibitors over nine days to bVSMCs

| Concentration | Potential inhibitor | Cell viability (%) | | | |
|---|---|---|---|---|---|
| | | no GAD | | with GAD | |
| | | mean | SD | mean | SD |
| — | NA | 100 | 0.71 | 73.41 | 1.83 |
| 10 μM | PJ | 98.3 | 2.25 | 69.43 | 5.71 |
| | MC | 105.1 | 2.87 | 105.89 | 17.23 |

TABLE 4-continued

Toxicity of medium only and GAD medium in combination with potential inhibitors over nine days to bVSMCs

| | | Cell viability (%) | | | |
| | | no GAD | | with GAD | |
| Concentration | Potential inhibitor | mean | SD | mean | SD |
| --- | --- | --- | --- | --- | --- |
| 1 μM | PJ | 97.1 | 1.01 | 59.06 | 8.71 |
|  | MC | 96.64 | 1.36 | 72.42 | 3.26 |
| 0.1 μM | PJ | 99.88 | 2.38 | 69.43 | 9.52 |
|  | MC | 98.51 | 0.63 | 74.53 | 2.78 |

Neither the NA-treatment nor the GAD-treatment was toxic to the bVSMCs after seven days.

After 9 days the matrix/cells which had been treated by the GAD medium started to roll up slightly inside the wells. The MTT assay showed a drop in formazan production of about 27% in the GAD-treatment group when compared to the NA-treatment group. This is most likely due to the rolling-up of the cells in the wells and reduced access/exposure to the cells to MTT rather than representing a drop in cell viability. This notion is supported by the fact that in the 10 μM MC-sample cells had rolled up considerably less and the drop off in formazan production in this treatment group was not observed.

Cresolphthalein Assay

Figure 12:
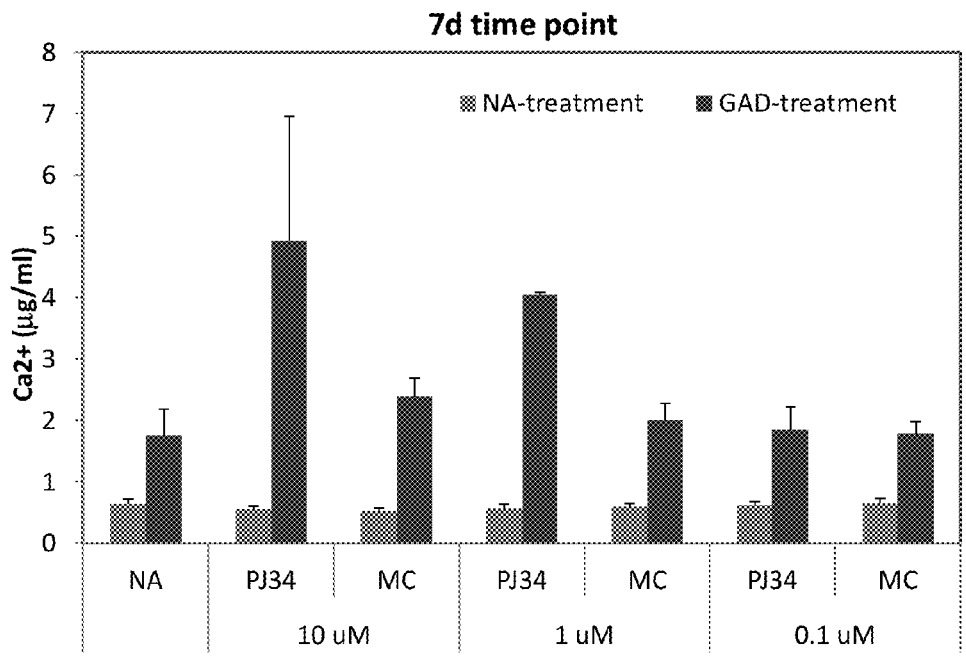
FIG. 12 is a graph showing the $Ca^{2+}$ concentration in a sample of bVSMCs which were incubated for 7 days with control medium (no GAD) or with β-GAD medium (with GAD) in the presence of no potential inhibitors (NA) or in the presence of PJ34 or minocycline (MC) at concentrations of 10 µM, 1 µM or 0.1 µM.

The $Ca^{2+}$ concentration results for the bVSMCs which were incubated for 7 days are given in Table 5, below, and shown graphically in FIG. 12. Similarly, $Ca^{2+}$ concentration results for the bVSMCs which were incubated for 9 days are given in Table 6, below, and shown graphically in FIG. 13. In each case, the values given represent the mean of triplicates. In FIGS. 12 and 13, error bars represent the standard deviation (SD) of the triplicates.

TABLE 5

$Ca^{2+}$ concentration found in bVSMCs grown in medium only and GAD medium in the presence of potential inhibitors over seven days

| | | μg calcium/ml | | | |
| | | no GAD | | with GAD | |
| Concentration | Potential inhibitor | mean | SD | mean | SD |
| --- | --- | --- | --- | --- | --- |
| — | NA | 0.647 | 0.076 | 1.75 | 0.44 |
| 10 μM | PJ34 | 0.561 | 0.048 | 4.93 | 2.03 |
|  | MC | 0.523 | 0.053 | 2.38 | 0.31 |
| 1 μM | PJ34 | 0.565 | 0.082 | 4.06 | 0.04 |
|  | MC | 0.595 | 0.055 | 2 | 0.28 |
| 0.1 μM | PJ34 | 0.612 | 0.07 | 1.84 | 0.39 |
|  | MC | 0.654 | 0.077 | 1.79 | 0.19 |

TABLE 6

$Ca^{2+}$ concentration found in bVSMCs grown in medium only and GAD medium in the presence of potential inhibitors over nine days

| | | μg calcium/ml | | | |
| | | no GAD | | with GAD | |
| Concentration | Potential inhibitor | mean | SD | mean | SD |
| --- | --- | --- | --- | --- | --- |
| — | NA | 1.363 | 0.175 | 26.7 | 17 |
| 10 μM | PJ34 | 1.061 | 0.281 | 66.68 | 5.83 |
|  | MC | 0.925 | 0.022 | 3.74 | 1.39 |

TABLE 6-continued $Ca^{2+}$ concentration found in bVSMCs grown in medium only and GAD medium in the presence of potential inhibitors over nine days

| | | μg calcium/ml | | | |
| | | no GAD | | with GAD | |
| Concentration | Potential inhibitor | mean | SD | mean | SD |
| --- | --- | --- | --- | --- | --- |
| 1 μM | PJ34 | 1.179 | 0.038 | 132.87 | 63.07 |
|  | MC | 1.327 | 0.159 | 21.35 | 9.69 |
| 0.1 μM | PJ34 | 1.438 | 0.057 | 22.69 | 13.16 |
|  | MC | 1.484 | 0.185 | 26.16 | 9.5 |

In the plates which were not treated with the GAD medium (identified as "NA-treatment" in FIGS. 12 and 13) the $Ca^{2+}$ content was very low after both 7 days and 9 days, as would be expected.

Where the plates were treated with the GAD medium the $Ca^{2+}$ concentration was only about three times higher than the $Ca^{2+}$ concentration of the plates not treated with the GAD medium after 7 days of treatment when no inhibitors were present, see the first two bars in FIG. 12. After 9 days however, a more dramatic increase in $Ca^{2+}$ concentration to about twenty five times more than that observed for the plates not treated with the GAD medium was observed when no inhibitors were present, see the first two bars in FIG. 13.

Figure 14:
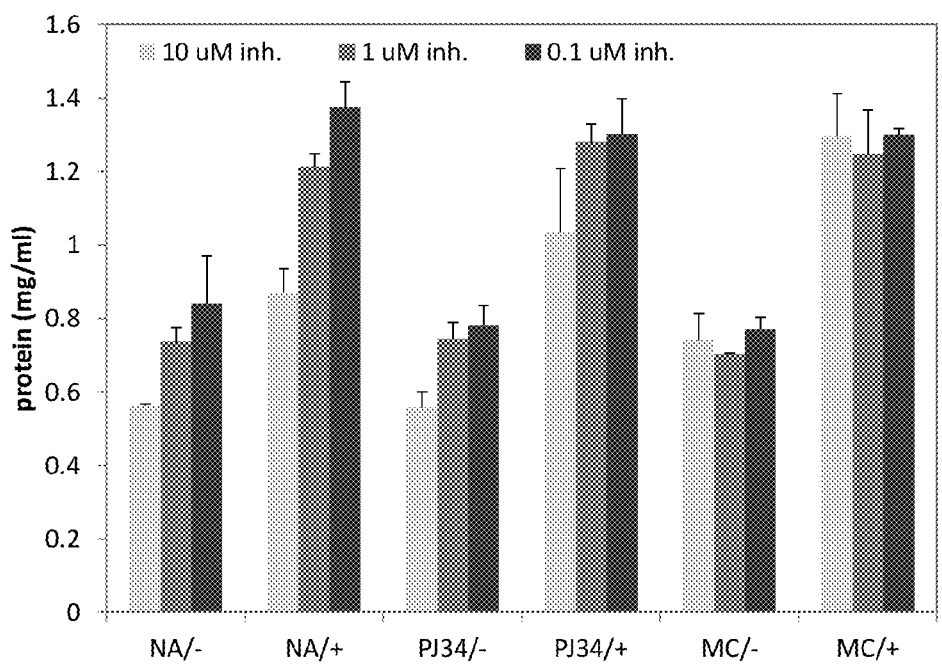
FIG. 14 is a graph showing total mass of protein in a sample of bVSMCs which were incubated for 7 days in control medium only (−) or with β-GAD medium (+) in the presence of no potential inhibitors (NA) or in the presence of PJ34 or minocycline (MC) at concentrations of 10 µM, 1 µM or 0.1 µM.
Figure 15:
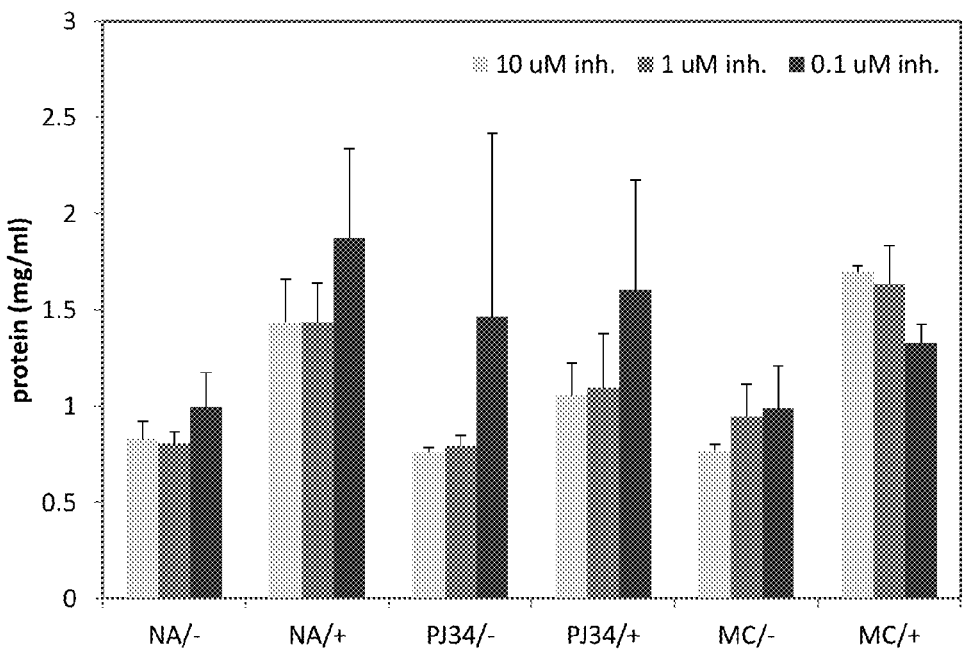
FIG. 15 is a graph showing total mass of protein in a sample of bVSMCs which were incubated for 9 days in control medium only (−) or with β-GAD medium (+) in the presence of no potential inhibitors (NA) or in the presence of PJ34 or minocycline (MC) at concentrations of 10 µM, 1 µM or 0.1 µM.

As discussed in example 4, when assessing the degree to which a compound inhibits calcification, it is usual in the literature to quantify the degree of inhibition of calcification as the mass of calcium in the sample per mass of protein in the sample. The total mass of protein in the sample was determined by the BioRad assay and is shown in FIGS. 14 and 15. In these Figures, the samples labelled with a "+" were treated with the GAD medium and the samples labelled "−" were not treated with the GAD medium.

Accordingly, it is clear that the total mass of protein is greater for the cell cultures treated with the GAD medium compared to those that were not treated with the GAD medium. However, GAD treatment does not cause any obvious change in number of cells in the sample, as determined by the MTT assay. Most likely, the increase in protein under GAD treatment compared to no GAD treatment is due to stimulation of extracellular matrix or other protein production.

Accordingly, the inventors believe that expressing the degree of calcification per milligram of protein overestimates any inhibitory effect by the trial inhibitors. To overcome this problem, the degree of calcification for plates treated with the GAD medium and a potential inhibitor was calculated as a percentage compared to the plates treated with the GAD medium and no inhibitor. These values are given in table 7 and shown graphically in FIG. 16.

TABLE 7

$Ca^{2+}$ concentration of bVSMCs grown in GAD medium over nine days with or without a potential inhibitor expressed as a percentage compared to plates grown in GAD medium over nine days without a potential inhibitor

| | | Ca2+ concentration (%) | |
| Concentration | Potential inhibitor | mean | SD |
| --- | --- | --- | --- |
| 10 μM | NA | 100 | 15.46 |
|  | PJ34 | 344.07 | 30.07 |
|  | MC | 19.3 | 7.17 |

TABLE 7-continued

Ca$^{2+}$ concentration of bVSMCs grown in GAD medium over nine days with or without a potential inhibitor expressed as a percentage compared to plates grown in GAD medium over nine days without a potential inhibitor

| Concentration | Potential inhibitor | Ca2+ concentration (%) | |
|---|---|---|---|
| | | mean | SD |
| 1 µM | NA | 100 | 34.59 |
| | PJ34 | 384.77 | 182.63 |
| | MC | 61.81 | 28.06 |
| 0.1 µM | NA | 100 | 110.11 |
| | PJ34 | 86.6 | 50.23 |
| | MC | 99.86 | 36.27 |

As noted in example 4, PJ-34 increased Ca$^{2+}$ deposition at concentrations of 10 µM. This effect is also observed at concentrations of 1 µM.

Minocycline reduced Ca$^{2+}$ deposition to ~19%, compared to when no potential inhibitor was present, at concentrations of 10 µM i.e. a reduction of about 81%. Similarly, minocycline reduced Ca$^{2+}$ deposition to ~62% compared to when no potential inhibitor was present, at concentrations of 1 µM, i.e. a reduction of about 38%. However, minocycline did not appear to have any effect on the concentration of Ca$^{2+}$ at concentrations of 0.1 µM.

Discussion

Minocycline shows a dose-dependent effect on calcification, consistent with this drug having a direct effect on the vascular calcification process. Accordingly, minocycline shows promise as an inhibitor of vascular calcification.

Advantageously, it is believed that minocycline could be used as an inhibitor of vascular calcification at a relatively low concentration which is within accepted safe levels.

Meanwhile, PJ-34 does appear to be encouraging calcification. However, it also appears to induce some cell death in bVSMCs, see FIG. 4A and example 2. Accordingly, it could be the cell death which causes the observed calcification.

A dead cell can (and usually will) act as a nidus for the precipitation of a mineral/calcification. It is unclear as to whether a similar process can happen around dead cells in vivo. However, in in vitro experiments, such as that discussed above, dead cells mean you see calcification. Accordingly, it is possible that PJ-34 might still be inhibiting calcification for the remaining live cells.

Example 6: Example Dose Suggestion

The experiments carried out in Example 5 showed that minocycline can inhibit calcification at concentrations as low as 1 µM, and could possibly be effective at lower concentrations too. The molecular mass of minocycline is 457 g/mol, so a concentration of 1 µM is equivalent to 0.46 micrograms/mL.

The maximum concentration (Cmax) of a 50 mg oral minocycline dose in a patient's bloodstream is 0.65 micrograms/mL reached 2 hours after dosing (Tmax).

Minocycline is typically taken twice per day, and the half-life of minocycline in the body is approximately 12 hours. The steady-state concentration of continuous 50 mg dose every 12 hours is therefore 1.3 micrograms/mL.

Accordingly, the dosage needed to reach the concentration of 0.46 micrograms/mL would be approximately 20 mg minocycline twice daily.

Minocycline side effects seem to be dose-dependent, and therefore should be surmountable at these low doses.

It should be noted that the adult dosage for minocycline to treat acne (its main use) is 50-100 mg twice daily and then moving on to a maintenance dose of 50-100 mg daily. Accordingly, the suggested dosage is within accepted safe levels.

Example 7: Initial Test on Vascular Calcification by PJ34, Minocycline and Cilostazol Using Human Vascular Smooth Muscle Cells (hVSMCs)

Methodology

Given the positive results and conclusions regarding inhibition of vascular calcification in an in-vitro bovine vascular smooth muscle cell model, the inventors continued their experiments in an in-vitro human vascular smooth muscle cell model.

Primary hVSMCs were cultured in M199 media containing FBS (M199/5% FBS). They were plated at a known cell density, allowed to grow for 24 hours and then treated with control (DMSO only) or calcification media (DMSO containing 2.7 mM Calcium+2.5 mM phosphate)+/−inhibitors. After 6 days, calcification was assessed using the o-Cresolphthalein assay for quantification of Ca$^{2+}$ deposition and a BioRad protein assay for protein content.

PJ34 was used at a concentration of 10 µM, while minocycline and cilostazol were both used at concentrations of 0.5 µM, 1 µM and 2 µM. Medium+/−inhibitors was exchanged every 2-3 days.

Figure 17:
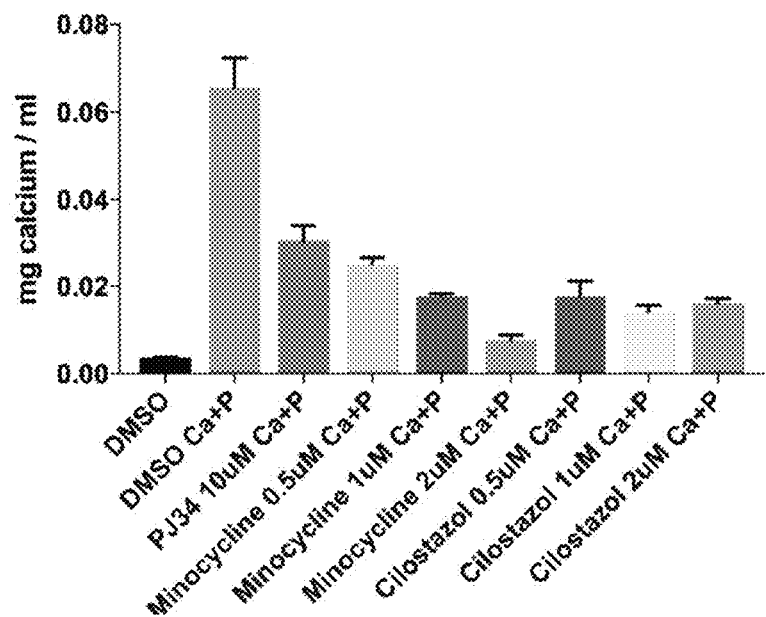
FIG. 17 is a graph showing the mass of calcium obtained from plates where human vascular smooth muscle cells (hVSMCs) were grown in the presence of DMSO only (negative control), DMSO+Ca/P (positive control for mineralization), or under mineralizing conditions in the presence of a PARP inhibitor (PJ-34, Minocycline or Cilostazol) at various concentrations.
Figure 18:
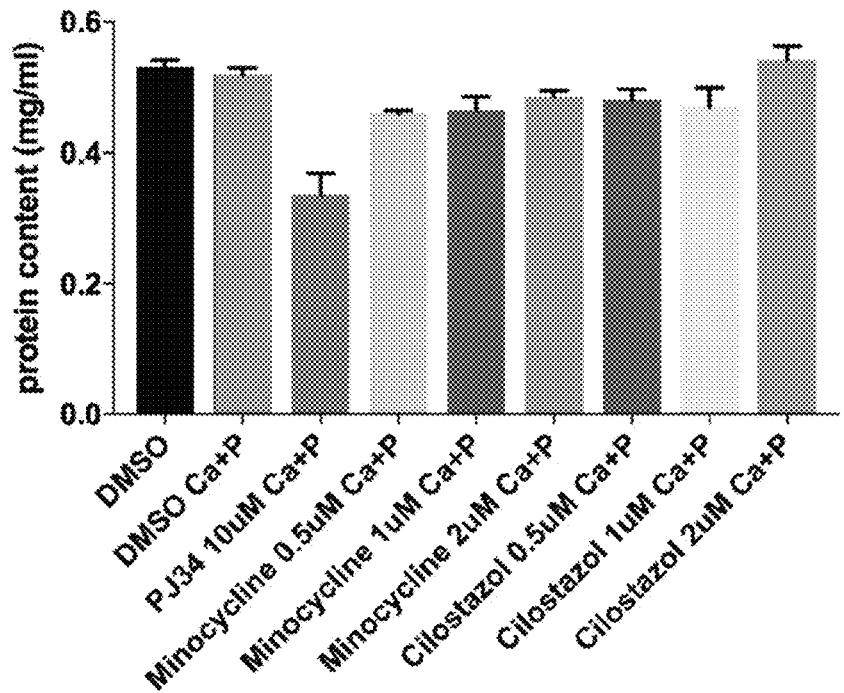
FIG. 18 is a graph showing the protein content for each of the plates where calcium content was given in FIG. 17.
Figure 19:
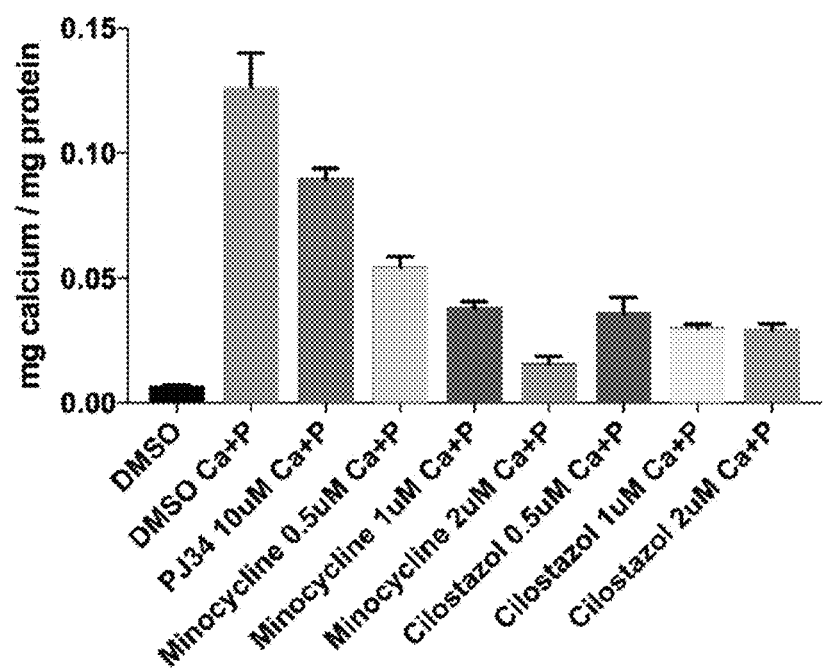
FIG. 19 is a graph which normalises the results shown in FIG. 17 to give the mass of calcium per mass of protein.

Each experiment was conducted in triplicate, and the FIGS. 17 to 19 show the mean+the standard error of the mean (SEM).

Results

The o-Cresolphthalein assay enabled the inventors to quantify the Ca$^{2+}$ deposition, as shown in FIG. 17. This showed that the calcium content in the DMSO group (negative control) was very low. Conversely, in the DMSO Ca+P group (positive control), the calcium levels were substantially elevated. PJ34, minocycline and cilostazol all appeared to reduce the calcium levels.

The results of the BioRad protein assay are shown in FIG. 18. The data obtained from this allowed the results obtained from the o-Cresolphthalein assay to be normalised, giving the mass of calcium per mass of protein. These normalised results are shown in FIG. 19.

As shown in FIG. 19, when the results are normalised, each of PJ34, minocycline and cilostazol lower calcium levels significantly. Additionally, minocycline appears to reduce calcium levels in a dose dependent manner.

Example 8: Further Tests on Vascular Calcification by PARP Inhibitors Using Human Vascular Smooth Muscle Cells (hVSMCs)

Methodology

Primary hVSMCs were cultured in M199 media containing FBS (M199/5% FBS). They were plated at a known cell density, allowed to grow for 24 hours and then treated with control (DMSO only) or calcification media (DMSO containing 2.7 mM Calcium+2.5 mM phosphate)+/−inhibitors. After 8 days, calcification was assessed using o-Cresolphthalein assay for quantification of Ca$^{2+}$ deposition and a BioRad protein assay for protein content.

The PARP inhibitors tested included olaparib (2 sources tested separately), talazoparib, niraparib, rucaparib and veliparib, along with minocycline and cilostazol. All of the compounds tested were used at a concentration of 3 µM. Medium+/−inhibitors was exchanged every 2-3 days.

Figure 20:
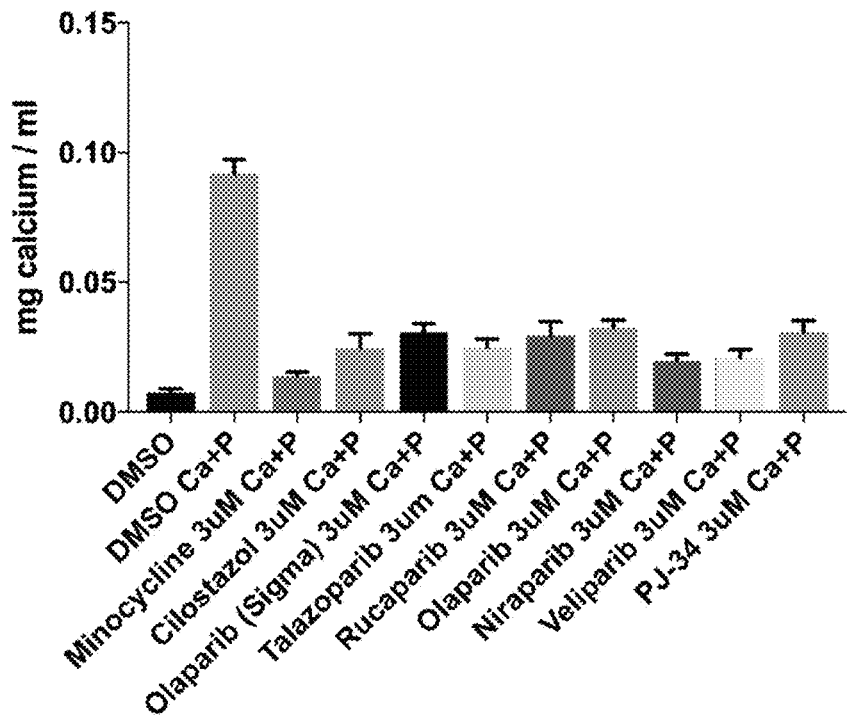
FIG. 20 is a graph showing the mass of calcium obtained from plates where human vascular smooth muscle cells (hVSMCs) were grown in the presence of DMSO only (negative control), DMSO+Ca/P (positive control for mineralization), or under mineralizing conditions in the presence of a PARP inhibitor (Minocycline, Cilostazol, Olaparib, Talazoparib, Rucaparib, Niraparib, Veliparib or PJ-34) at a concentration of 3 µM.
Figure 22:
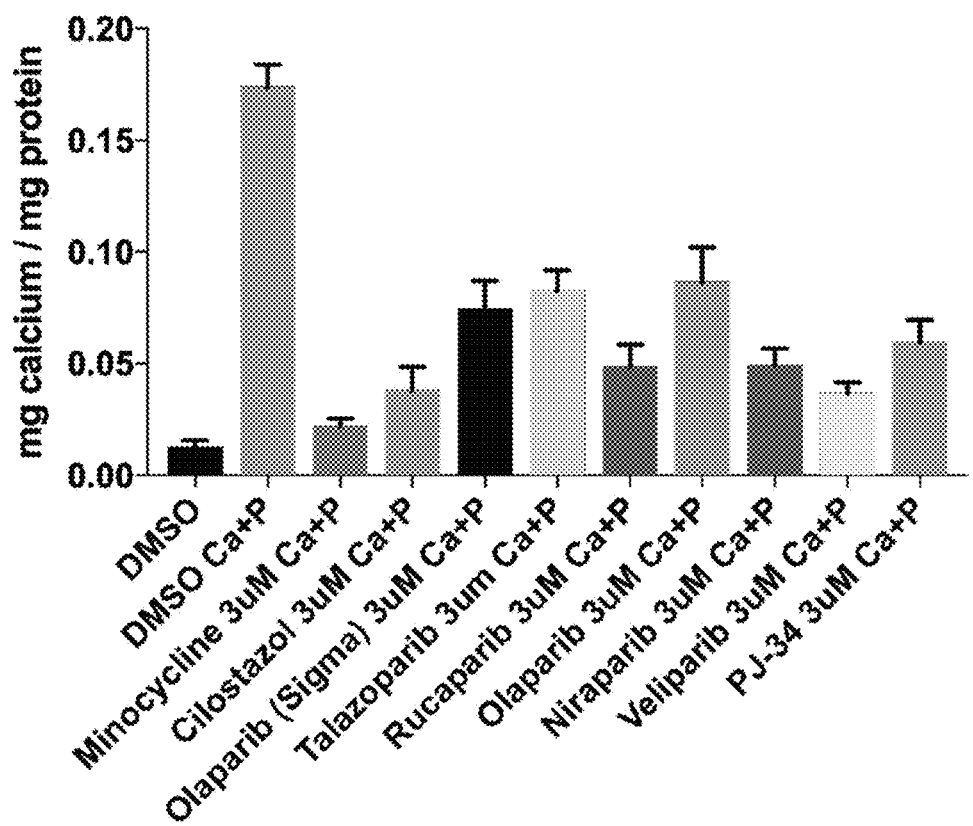
FIG. 22 is a graph which normalises the results shown in FIG. 20 to give the mass of calcium per mass of protein.

Each experiment was conducted six times, and FIGS. 20 and 22 show the mean+the standard error of the mean (SEM).

Results

Figure 23:
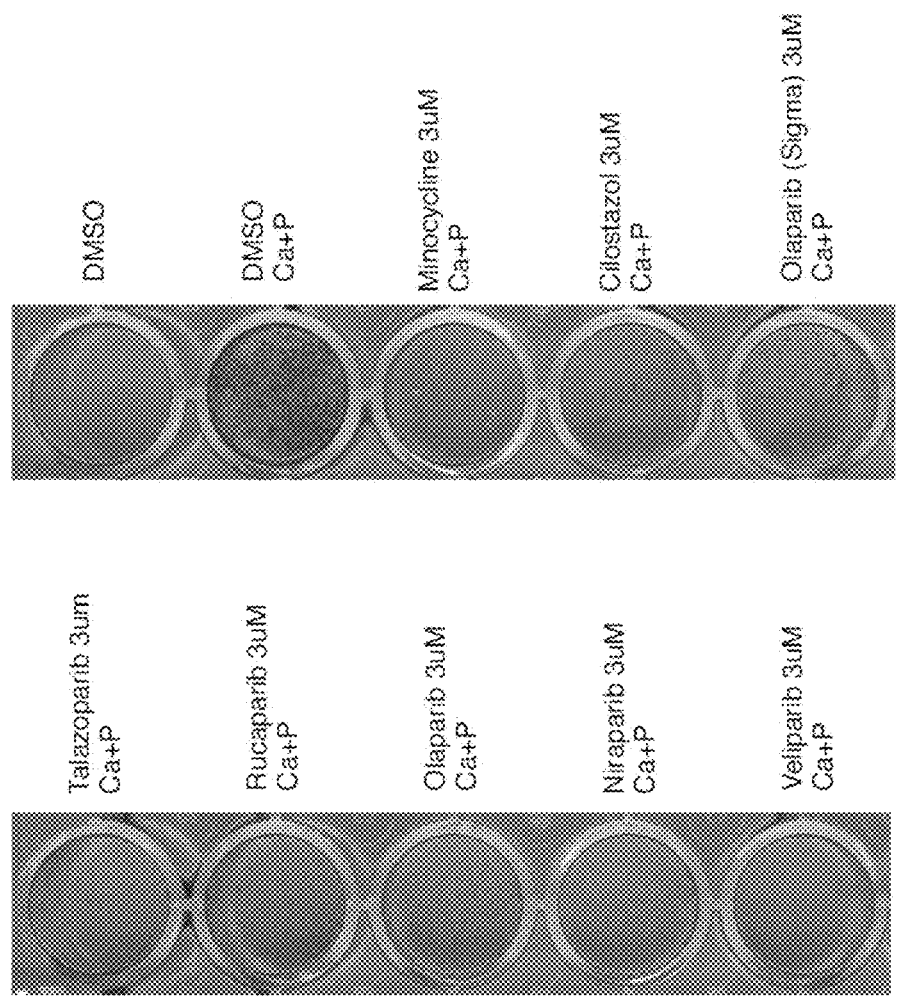
FIG. 23 shows the results obtained using Alizarin Red S staining for each of the plates where calcium content was given in FIG. 20.
Figure 24:
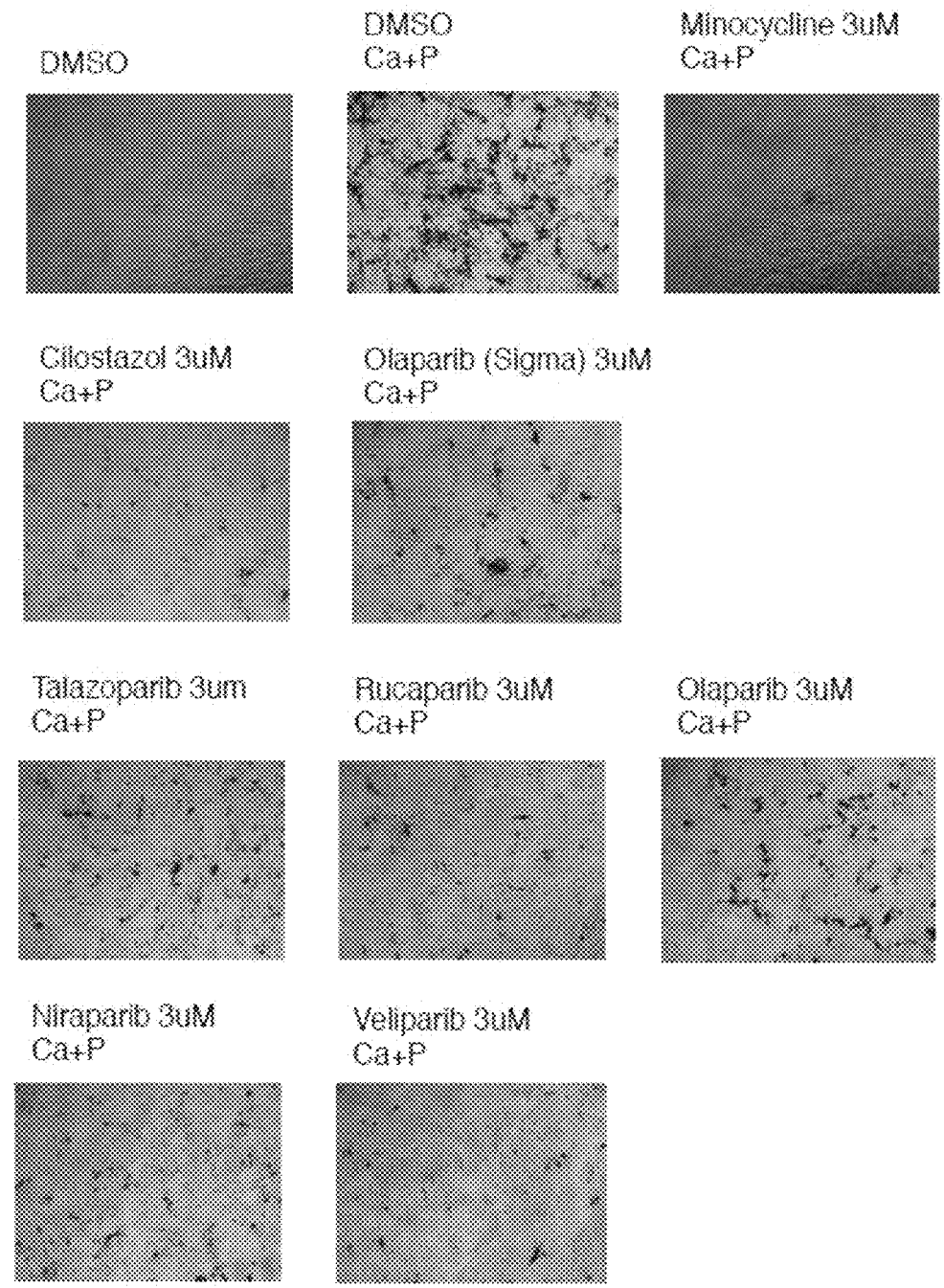
FIG. 24 shows a close up photograph for each of the plates where calcium content was given in FIG. 20.

Close up photographs of the plates are shown in FIG. 24, and photographs of the plates treated with Alizarin Red S staining is shown in FIG. 23. It is clear that for the cells in the DMSO group (negative control) there is minimal calcification, and minimal red staining due to Alizarin is visible in FIG. 23. This indicates that little or no calcification of the culture had taken place.

In contrast, the images show that a large amount of calcification occurred for the cells in the DMSO Ca+P group (positive control). While a degree of calcification occurred for all of the cell cultures treated with PARP inhibitors, it is clear that this is significantly less than for the cells in the DMSO Ca+P group.

The o-Cresolphthalein assay enabled the inventors to quantify the $Ca^{2+}$ deposition, as shown in FIG. 20. As with example 7, the calcium content in the DMSO group (negative control) was very low and the calcium content in the DMSO Ca+P group (positive control) was substantially elevated. All of the PARP inhibitors appeared to reduce the calcium levels.

Figure 21:
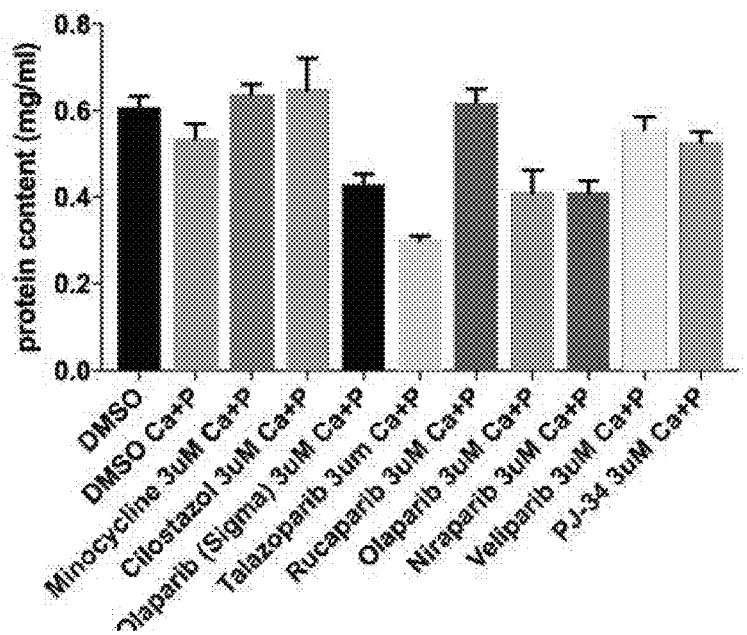
FIG. 21 is a graph showing the protein content for each of the plates where calcium content was given in FIG. 20.

The results of the BioRad protein assay are shown in FIG. 21. The data obtained from this allowed the results obtained from the o-Cresolphthalein assay to be normalised, giving the mass of calcium per mass of protein. These normalised results are shown in FIG. 22.

As shown in FIG. 22, when the results are normalised, all of the PARP inhibitors lower calcium levels significantly. Minocycline, cilostazol, rucaparib, niraparib and veliparib were particularly effective at lowering the calcium levels.

Example 9: Further Tests on Vascular Calcification by PARP Inhibitors Using Human Vascular Smooth Muscle Cells (hVSMCs)

Methodology

Primary hVSMCs were cultured in M199 media containing FBS (M199/5% FBS). They were plated at a known cell density, allowed to grow for 24 hours and then treated with control (DMSO only) or calcification media (DMSO containing 2.7 mM Calcium+2.5 mM phosphate)+/−compounds. After 8 days, calcification was assessed using o-Cresolphthalein assay for quantification of $Ca^{2+}$ deposition and a BioRad protein assay for protein content.

Alongside the DMSO negative control and DMSO Ca+P positive control, the following compounds were tested in this experiment: Bosentan monohydrate, pentoxifylline, losartan, amlodipine, atorvastatin, veliparib, minocycline and cilostazol.

Bosentan monohydrate and pentoxifylline were included as examples of existing drugs originally examined to check PARP inhibitor characteristics in the bovine VSMC model with negative results (Example 4). Losartan, amlodipine and atorvastatin were included as examples of common cardiovascular drugs (angiotensin II antagonist, calcium channel blocker and statin respectively) to check whether they inhibited medial vascular calcification. Veliparib was included as an example of a known PARP inhibitor that was shown in Example 8 to inhibit calcification. Minocycline was included given the positive experimental results throughout the bovine VSMC model and human VSMC model work (shown in Examples 4-8). Cilostazol was included given the positive experimental results in the human VSMC work (shown in Examples 7 and 8).

The compounds were used at concentrations of between 0.05 µM and 3 µM, as indicated in the Figures. These concentrations were chosen to mimic the systemic concentrations of these drugs following patient dosing according to the dose schedule in the prescribing information for each drug. Medium+/−inhibitors was exchanged every 2-3 days.

Figure 25:
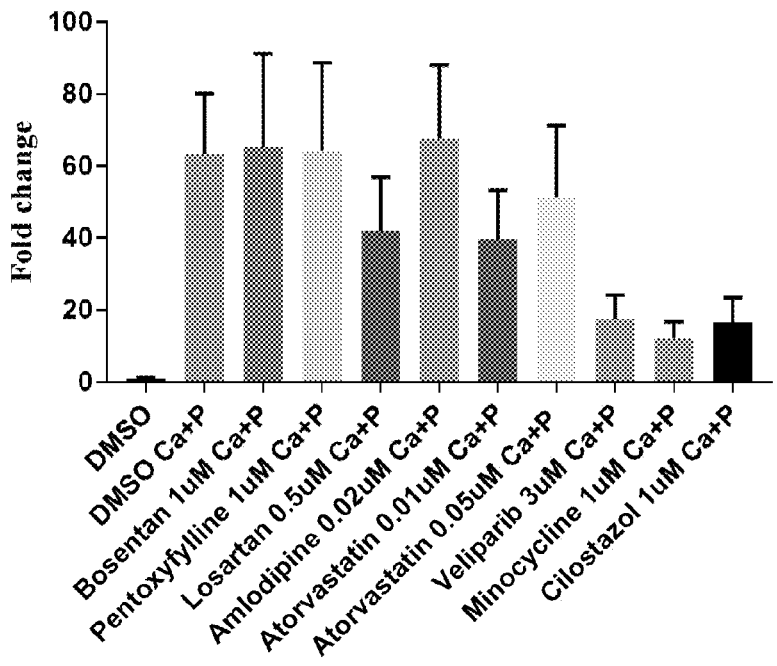
FIG. 25 is a graph showing the mass of calcium obtained from plates where human vascular smooth muscle cells (hVSMCs) were grown in the presence of DMSO only (negative control), DMSO+Ca/P (positive control for mineralization), or under mineralizing conditions in the presence of a PARP inhibitor (Veliparib, Minocycline or Cilostazol) or another drug (Bosentan, Pentoxyifylline, Losartan, Amlodipine or Atorvastatin) at various concentrations, as indicated on the graph.
Figure 26:
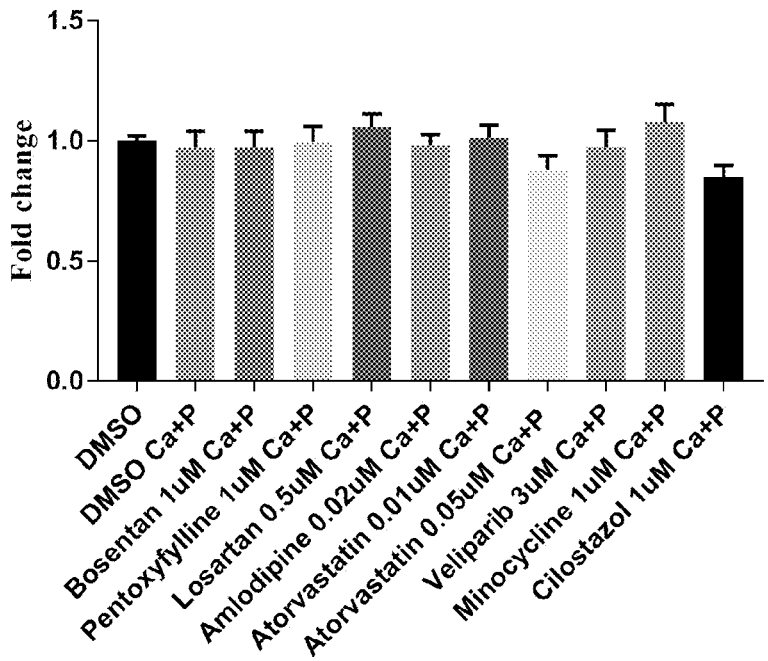
FIG. 26 is a graph showing the protein content for each of the plates where calcium content was given in FIG. 25.
Figure 27:
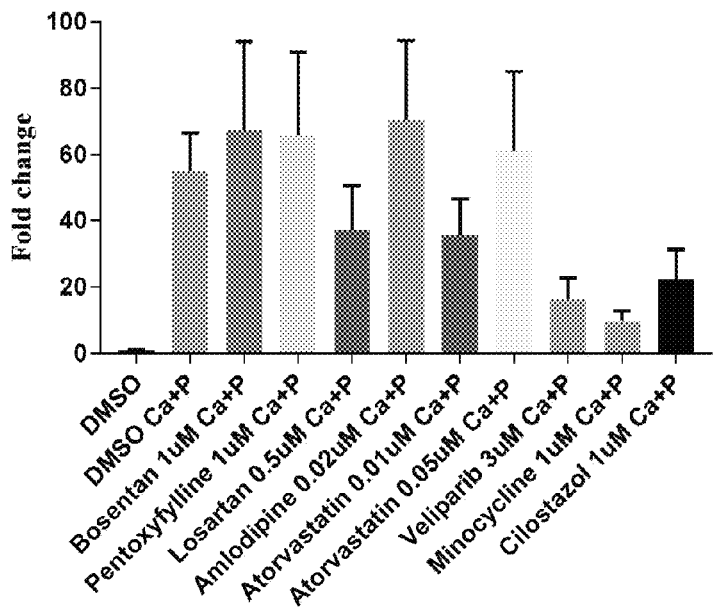
FIG. 27 is a graph which normalises the results shown in FIG. 25 to give the mass of calcium per mass of protein.
Figure 28A:
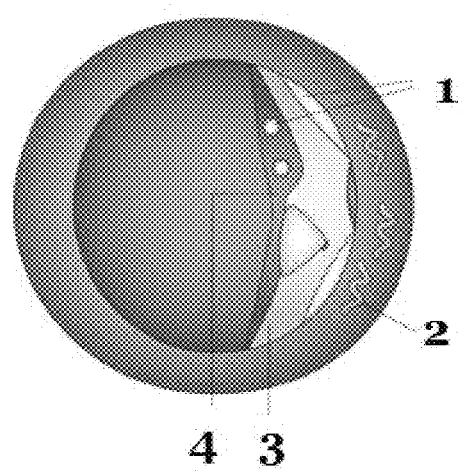
FIG. 28A shows atherosclerotic calcification.
Figure 28B:
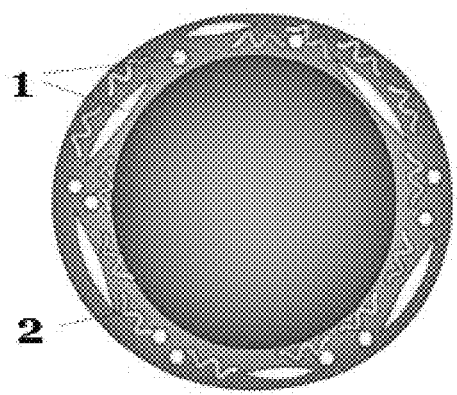
FIG. 28B shows medial calcification.

Each experiment was conducted three times, and the FIGS. 25 to 27 show the mean+the standard error of the mean (SEM).

Results

The o-Cresolphthalein assay enabled the inventors to quantify the $Ca^{2+}$ deposition, as shown in FIG. 25. This showed that the calcium content in the DMSO group (negative control) was very low. Conversely, in the DMSO Ca+P group (positive control), the calcium levels were substantially elevated.

The results of the BioRad protein assay are shown in FIG. 26. The data obtained from this allowed the results obtained from the o-Cresolphthalein assay to be normalised, giving the mass of calcium per mass of protein. These normalised results are shown in FIG. 27.

FIG. 27 shows the normalised results. Veliparib, minocycline and cilostazol each inhibit calcification significantly and repeatedly (narrow error bars). The results confirm that bosentan monohydrate and pentoxifylline do not inhibit calcification. Importantly, the results also confirm that example common cardiovascular drugs (losartan, amlodipine and atorvastatin) also do not inhibit medial vascular calcification. The error bars show the wide variation of results seen with bosentan monohydrate, pentoxifylline, losartan, amlodipine and atorvastatin.

SUMMARY

The results show a strong spatial correlation between extracellular poly(ADP ribose) and calcified regions of the extracellular matrix in both developing bone and pathological vascular calcification, suggesting there is likely to be a direct mechanistic relationship between poly(ADP ribose) and the construction of calcification deposits within the extracellular matrix.

Vascular smooth muscle cells express many osteogenic proteins when they calcify their matrix, including bone sialoprotein, osteopontin and osteocalcin and so a similar poly(ADP ribose)-mediated construction process could occur in vascular calcification too.

The inventors have shown that all known PARP inhibitors tested (olaparib, rucaparib, niraparib, veliparib and talazoparib) together with minocycline and cilostazol significantly reduce extracellular matrix calcification in bovine cell and human cell in vitro vascular calcification model. This suggests a potential route to reduce medial vascular calcification in vivo. Through the negative results obtained testing examples of other cardiovascular drugs (notably including a statin) the inventors have ruled out that patients are already receiving a medial vascular calcification inhibitory effect from other commonly prescribed cardiovascular medication.

Since the compounds above were able to inhibit calcification at low concentrations in vitro this indicates that a drug for inhibiting medial vascular calcification could be useful at low dosages, which ensures that side effects should be surmountable.

The invention claimed is:

1. A method of treating or ameliorating medial vascular calcification or intimal atherosclerotic calcification in a subject, the method comprising administering to a subject in need of such treatment, a therapeutically effective amount of a poly(ADP ribose) polymerase (PARP) inhibitor and/or a tetracycline, or a pharmaceutically acceptable salt or solvate thereof.

2. A method according to claim 1, wherein the method is a method of treating or ameliorating medial vascular calcification.

3. A method according to claim 2, wherein the method is a method of treating or ameliorating Mönckeberg's arteriosclerosis or calcific uremic arteriolopathy (CUA).

4. A method according to claim 2, wherein the subject is suffering from chronic kidney disease, diabetes, ageing, hyperparathyroidism, hyperphosphatemia, a vitamin D disorder, a vitamin K disorder, osteoporosis, Kawasaki disease, arterial calcification due to deficiency of CD73 (ACDC), generalized arterial calcification of infancy (GACI), idiopathic basal ganglia calcification (IBGC), pseudoxanthoma elasticum (PXE), rheumatoid arthritis, Singleton-Merten syndrome and/or β-thalassemia.

5. A method according to claim 1, wherein the method is a method of treating or ameliorating intimal atherosclerotic calcification.

6. A method according to claim 5, wherein the subject has an Agatston score of at least 20, at least 40, at least 60, at least 80 or at least 100.

7. A method according to claim 1, wherein the PARP inhibitor and/or tetracycline is a PARP inhibitor and is selected from a group consisting of: olaparib; rucaparib; niraparib; veliparib; talazoparib; minocycline; cilostazol; N-(6-Oxo-5,6-dihydrophenanthridin-2-yl)-(N,N-dimethylamino) acetamide hydrochloride (PJ34); 3-aminobenzamide (3-AB); and 3,4-dihydro-5-[4-(1-piperidinyl)butoxyl]-1 (2H)-isoquinolinone (DPQ), or a derivative thereof.

8. A method according to claim 7, wherein the PARP inhibitor is selected from a group consisting of olaparib; rucaparib; niraparib; veliparib; talazoparib; minocycline; and cilostazol, or a derivative thereof.

9. A method according to claim 1, wherein the PARP inhibitor and/or tetracycline is a tetracycline and is selected from a group consisting of: tetracycline; chlortetracycline; oxytetracycline; demeclocycline; lymecycline; meclocycline; metacycline; minocycline; rolitetracycline; doxycycline; tigecycline; clomocycline; and pipacycline.

10. A method according to claim 9, wherein the tetracycline is minocycline.

11. A method according to claim 1, wherein the PARP inhibitor and/or tetracycline is administered as a daily dose of between 1 mg and 10000 mg or between 2 mg and 2000 mg, between 5 mg and 1000 mg, between 10 mg and 200 mg, between 15 mg and 100 mg or between 20 mg and 50 mg.

12. A method according to claim 1, wherein the PARP inhibitor and/or tetracycline is administered as two daily doses, wherein each dose is between 1 mg and 5000 mg, between 2 mg and 1000 mg, between 3 mg and 500 mg, between 4 mg and 100 mg, between 5 mg and 50 mg or between 10 mg and 25 mg.

13. A method according to claim 12, wherein each dose is between 10 mg and 25 mg.

* * * * *